(12) United States Patent
Patel et al.

(10) Patent No.: US 11,498,165 B2
(45) Date of Patent: Nov. 15, 2022

(54) SYSTEMS AND METHODS FOR TREATING ANEURYSMS

(71) Applicant: Covidien LP, Mansfield, MA (US)

(72) Inventors: Gopan Patel, Orange, CA (US); Mark Ashby, Laguna Niguel, CA (US); Kenneth Brown, Oceanside, CA (US); Erik Skillrud, Irvine, CA (US); Junwei Li, Irvine, CA (US)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 16/949,563

(22) Filed: Nov. 3, 2020

(65) Prior Publication Data
US 2021/0128167 A1    May 6, 2021

Related U.S. Application Data

(60) Provisional application No. 62/930,357, filed on Nov. 4, 2019, provisional application No. 62/930,324, filed
(Continued)

(51) Int. Cl.
*A61B 17/12* (2006.01)
*B23P 19/04* (2006.01)
(Continued)

(52) U.S. Cl.
CPC ........ *B23P 19/047* (2013.01); *A61B 17/1214* (2013.01); *A61B 17/12031* (2013.01);
(Continued)

(58) Field of Classification Search
CPC ........ A61B 17/12031; A61B 17/12113; A61B 17/1214; A61B 17/12145;
(Continued)

(56) References Cited

U.S. PATENT DOCUMENTS 5,261,916 A    11/1993    Engelson
5,601,600 A    2/1997    Ton
(Continued)

FOREIGN PATENT DOCUMENTS

CA    3031482 A1    8/2017
CN    105105812 A    12/2015
(Continued)

OTHER PUBLICATIONS

International Search Report and Written Opinion dated Feb. 23, 2021, International Application No. PCT/US20/70743, 14 pages.
(Continued)

*Primary Examiner* — Katherine M Shi
*Assistant Examiner* — Paige A Codrington
(74) *Attorney, Agent, or Firm* — Fortem IP LLP; Matthew Lincicum

(57) ABSTRACT

Treatment of aneurysms can be improved by delivering an occlusive member (e.g., an expandable braid) to an aneurysm sac in conjunction with an embolic element (e.g., coils, embolic material). A delivery system for such treatment can include an occlusive member configured to be positioned within an aneurysm sac and having a proximal hub. An elongate tubular member has an engagement member removably coupled to the proximal hub, for example via threaded engagement or an interference fit via one or more engagement members. A conduit extending within or adjacent to the elongated member is configured to receive an embolic element therethrough for delivery to the aneurysm sac.

19 Claims, 14 Drawing Sheets

Related U.S. Application Data on Nov. 4, 2019, provisional application No. 62/930,421, filed on Nov. 4, 2019, provisional application No. 62/930,303, filed on Nov. 4, 2019, provisional application No. 62/930,487, filed on Nov. 4, 2019, provisional application No. 62/930,333, filed on Nov. 4, 2019.

(51) Int. Cl.
*A61B 17/00* (2006.01)
*A61B 90/00* (2016.01)

(52) U.S. Cl.
CPC .. *A61B 17/12113* (2013.01); *A61B 17/12145* (2013.01); *A61B 17/12172* (2013.01); *A61B 17/12186* (2013.01); *A61B 17/12168* (2013.01); *A61B 2017/00526* (2013.01); *A61B 2017/00557* (2013.01); *A61B 2017/00862* (2013.01); *A61B 2017/00929* (2013.01); *A61B 2017/12054* (2013.01); *A61B 2017/12063* (2013.01); *A61B 2090/376* (2016.02); *A61B 2090/3966* (2016.02)

(58) Field of Classification Search
CPC ........ A61B 17/12172; A61B 17/12186; A61B 17/12168; A61B 17/12181; A61B 17/0057; A61B 2017/00526; A61B 2017/00557; A61B 2017/00862; A61B 2017/00929; A61B 2017/12054; A61B 2017/12063; A61B 2017/1209; A61B 2017/00575; A61B 2017/00623; A61B 2017/00632; A61B 2090/376; A61B 2090/3966; A61F 2/011; A61F 2/2427; A61F 2002/9505
USPC ........................................................ 606/191
See application file for complete search history.

(56) References Cited

U.S. PATENT DOCUMENTS

| | | | |
|---|---|---|---|
| 5,916,235 A | 6/1999 | Guglielmi | |
| 6,936,058 B2* | 8/2005 | Forde | A61F 2/962 606/200 |
| 7,128,736 B1 | 10/2006 | Abrams et al. | |
| 7,473,266 B2* | 1/2009 | Glaser | A61B 17/0057 606/200 |
| 7,879,065 B2* | 2/2011 | Gesswein | A61F 2/01 606/200 |
| 8,690,936 B2* | 4/2014 | Nguyen | A61F 2/2436 623/1.11 |
| 9,339,275 B2* | 5/2016 | Trommeter | A61B 17/12031 |
| 9,713,475 B2* | 7/2017 | Divino | A61B 17/12168 |
| 9,918,718 B2* | 3/2018 | Lorenzo | A61B 17/1214 |
| 10,932,933 B2* | 3/2021 | Bardsley | A61B 17/12145 |
| 10,952,740 B2 | 3/2021 | Dasnurkar et al. | |
| 11,076,860 B2 | 8/2021 | Lorenzo | |
| 11,134,953 B2 | 10/2021 | Solaun | |
| 11,179,159 B2 | 11/2021 | Cox et al. | |
| 2001/0000797 A1 | 5/2001 | Mazzocchi | |
| 2004/0176798 A1* | 9/2004 | Epstein | A61B 17/12022 606/213 |
| 2004/0236344 A1 | 11/2004 | Monstadt et al. | |
| 2005/0038470 A1* | 2/2005 | van der Burg | A61B 17/0057 606/213 |
| 2005/0119684 A1 | 6/2005 | Guterman et al. | |
| 2006/0064151 A1 | 3/2006 | Guterman et al. | |
| 2006/0276824 A1 | 12/2006 | Mitelberg et al. | |
| 2006/0276829 A1 | 12/2006 | Balgobin et al. | |
| 2007/0179520 A1 | 8/2007 | West | |
| 2007/0186933 A1 | 8/2007 | Domingo et al. | |
| 2007/0198075 A1 | 8/2007 | Levy | |
| 2007/0221230 A1 | 9/2007 | Thompson et al. | |
| 2007/0299461 A1 | 12/2007 | Elliott | |
| 2008/0119886 A1* | 5/2008 | Greenhalgh | A61B 17/12022 606/200 |
| 2008/0221554 A1 | 9/2008 | Oconnor et al. | |
| 2008/0221703 A1 | 9/2008 | Que et al. | |
| 2008/0281350 A1 | 11/2008 | Sepetka et al. | |
| 2008/0283066 A1 | 11/2008 | Delgado et al. | |
| 2009/0036877 A1 | 2/2009 | Nardone et al. | |
| 2009/0099592 A1 | 4/2009 | Buiser et al. | |
| 2009/0287294 A1* | 11/2009 | Rosqueta | A61B 17/12113 623/1.15 |
| 2010/0023048 A1 | 1/2010 | Mach | |
| 2010/0121350 A1 | 5/2010 | Mirigian | |
| 2011/0144669 A1* | 6/2011 | Becking | A61B 17/12172 606/158 |
| 2011/0238041 A1 | 9/2011 | Lim et al. | |
| 2012/0123510 A1 | 5/2012 | Liungman | |
| 2012/0143301 A1 | 6/2012 | Maslanka et al. | |
| 2013/0066357 A1* | 3/2013 | Aboytes | A61B 17/12172 606/198 |
| 2013/0073026 A1 | 3/2013 | Russo et al. | |
| 2013/0138136 A1 | 5/2013 | Beckham et al. | |
| 2013/0211495 A1 | 8/2013 | Halden et al. | |
| 2014/0039542 A1* | 2/2014 | Trommeter | A61B 17/12109 606/200 |
| 2014/0135811 A1 | 5/2014 | Divino et al. | |
| 2014/0200607 A1 | 7/2014 | Sepetka et al. | |
| 2014/0215792 A1 | 8/2014 | Leopold et al. | |
| 2014/0257360 A1 | 9/2014 | Keillor | |
| 2015/0005808 A1 | 1/2015 | Chouinard et al. | |
| 2015/0272589 A1 | 10/2015 | Lorenzo | |
| 2015/0313605 A1 | 11/2015 | Griffin | |
| 2015/0335333 A1* | 11/2015 | Jones | A61B 17/12154 606/200 |
| 2015/0343181 A1* | 12/2015 | Bradway | A61B 17/12031 604/103.1 |
| 2016/0022445 A1* | 1/2016 | Ruvalcaba | A61F 2/82 606/198 |
| 2016/0106437 A1 | 4/2016 | Van Der Burg et al. | |
| 2016/0128699 A1* | 5/2016 | Hadley | A61F 2/0108 606/200 |
| 2016/0331381 A1 | 11/2016 | Ma | |
| 2017/0105739 A1 | 4/2017 | Dias et al. | |
| 2017/0156734 A1 | 6/2017 | Griffin | |
| 2017/0224350 A1 | 8/2017 | Shimizu et al. | |
| 2017/0354421 A1* | 12/2017 | Maguire | A61B 17/12109 |
| 2017/0367713 A1 | 12/2017 | Greene et al. | |
| 2018/0070955 A1 | 3/2018 | Greene et al. | |
| 2018/0110797 A1 | 4/2018 | Li et al. | |
| 2018/0132856 A1 | 5/2018 | Wierzbicki et al. | |
| 2018/0140305 A1 | 5/2018 | Connor | |
| 2018/0206852 A1 | 7/2018 | Moeller | |
| 2018/0242979 A1* | 8/2018 | Lorenzo | A61B 17/12031 |
| 2018/0256171 A1 | 9/2018 | Chow et al. | |
| 2018/0317932 A1 | 11/2018 | H'Doubler | |
| 2019/0008522 A1* | 1/2019 | Lorenzo | A61B 17/12172 |
| 2019/0009057 A1 | 1/2019 | Li et al. | |
| 2019/0053807 A1 | 2/2019 | Tassoni et al. | |
| 2019/0223876 A1 | 7/2019 | Badruddin et al. | |
| 2019/0223881 A1 | 7/2019 | Hewitt et al. | |
| 2019/0343532 A1 | 11/2019 | Divino et al. | |
| 2019/0351107 A1 | 11/2019 | Sawhney et al. | |
| 2020/0138448 A1 | 5/2020 | Dasnurkar et al. | |
| 2020/0268392 A1 | 8/2020 | Choi et al. | |
| 2021/0128160 A1 | 5/2021 | Li et al. | |
| 2021/0128161 A1 | 5/2021 | Nageswaran et al. | |
| 2021/0128162 A1 | 5/2021 | Rhee et al. | |
| 2021/0128165 A1 | 5/2021 | Pulugurtha et al. | |
| 2021/0128168 A1 | 5/2021 | Nguyen et al. | |
| 2021/0128169 A1 | 5/2021 | Li et al. | |
| 2021/0129275 A1 | 5/2021 | Nguyen et al. | |
| 2021/0153872 A1 | 5/2021 | Nguyen et al. | |
| 2021/0161643 A1 | 6/2021 | Totten et al. | |

(56) References Cited

U.S. PATENT DOCUMENTS

2021/0196284 A1    7/2021  Gorochow et al.
2021/0212698 A1*  7/2021  Connor .............. A61B 17/1214

FOREIGN PATENT DOCUMENTS

| WO | 9905977 A1 | 2/1999 |
| WO | 93011151 A1 | 2/2003 |
| WO | 2015166013 A1 | 11/2015 |
| WO | 2018050262 A1 | 3/2018 |
| WO | 2019038293 A1 | 2/2019 |

OTHER PUBLICATIONS

International Search Report and Written Opinion dated Apr. 13, 2021, International Application No. PCT/US20/70742, 18 pages.
International Search Report and Written Opinion dated Feb. 17, 2021, International Application No. PCT/US20/70741, 6 pages.

* cited by examiner

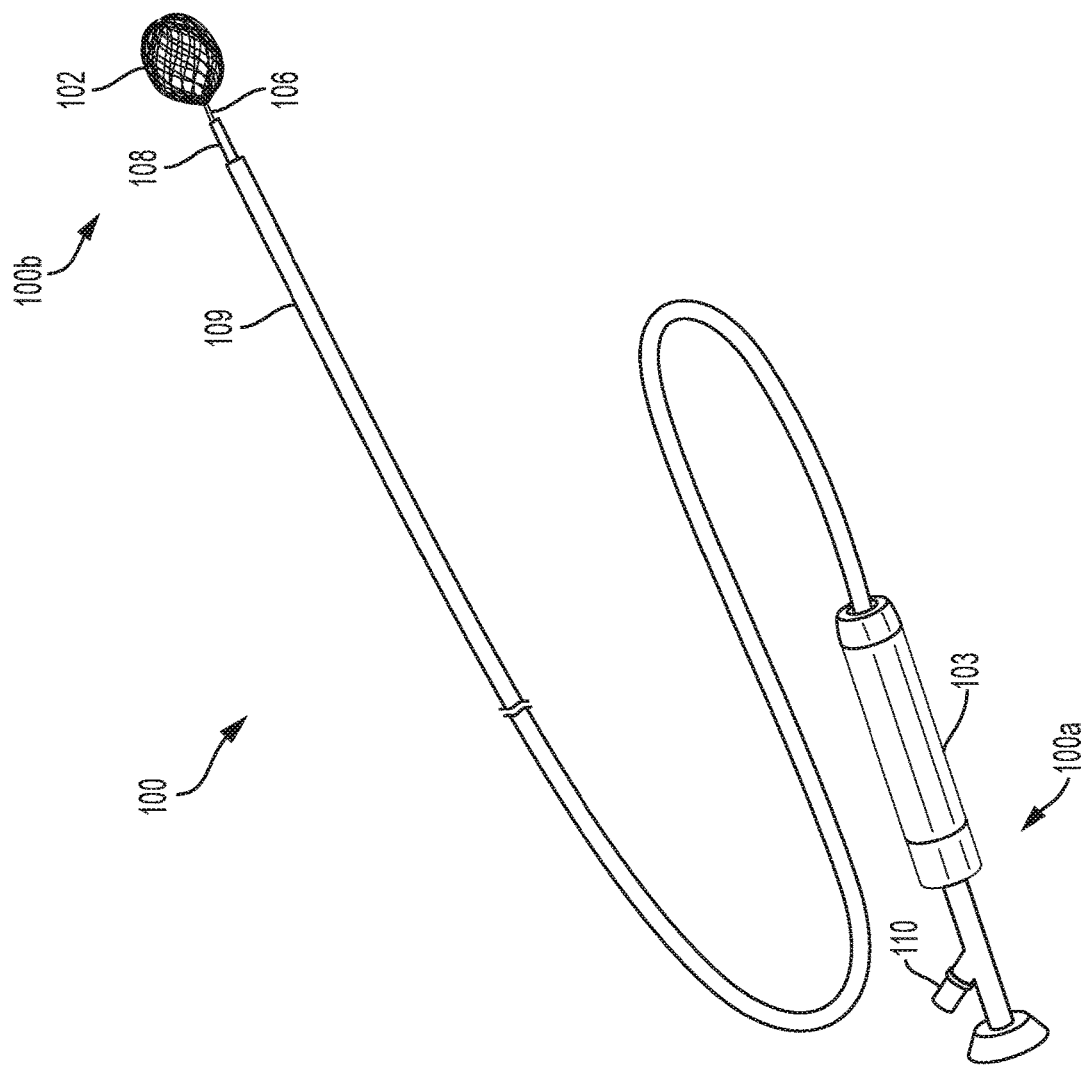

SYSTEMS AND METHODS FOR TREATING ANEURYSMS

CROSS-REFERENCE TO RELATED APPLICATIONS

The present application claims the benefit of priority of U.S. Provisional Application No. 62/930,421, filed Nov. 4, 2019, U.S. Provisional Application No. 62/930,487, filed Nov. 4, 2019, U.S. Provisional Application No. 62/930,303, filed Nov. 4, 2019, U.S. Provisional Application No. 62/930,324, filed Nov. 4, 2019, U.S. Provisional Application No. 62/930,333, filed Nov. 4, 2019, and U.S. Provisional Application No. 62/930,357, filed Nov. 4, 2019, each of which is incorporated by reference herein in its entirety.

The following applications are also incorporated by reference herein in their entireties: U.S. patent application Ser. No. 16/949,567, filed concurrently herewith, and titled DEVICES, SYSTEMS, AND METHODS FOR TREATMENT OF INTRACRANIAL ANEURYSMS; U.S. patent application Ser. No. 16/949,568, filed concurrently herewith, and titled DEVICES, SYSTEMS, AND METHODS FOR TREATING of INTRACRANIAL ANEURYSMS; U.S. patent application Ser. No. 16/949,561, filed concurrently herewith, and titled SYSTEMS AND METHODS FOR TREATING ANEURYSMS; U.S. patent application Ser. No. 16/949,564, filed concurrently herewith, and titled SYSTEMS AND METHODS FOR TREATING ANEURYSMS; U.S. patent application Ser. No. 16/949,565 filed concurrently herewith, and titled ANEURYSM TREATMENT DEVICE; U.S. patent application Ser. No. 16/949,569, filed concurrently herewith, and titled DEVICES, SYSTEMS, AND METHODS FOR TREATING OF INTRACRANIAL ANEURYSMS; U.S. patent application Ser. No. 16/949,566 filed concurrently herewith, and titled SYSTEMS AND METHODS FOR TREATING ANEURYSMS; and U.S. patent application Ser. No. 16/949,570, filed concurrently herewith, and titled DEVICES, SYSTEMS, AND METHODS FOR TREATING ANEURYSMS; and International Application No. PCT/US2020/070743, filed concurrently herewith, titled DEVICES, SYSTEMS, AND METHODS FOR TREATMENT OF INTRACRANIAL ANEURYSMS; International Application No. PCT/US2020/070741, filed concurrently herewith, titled DEVICES SYSTEMS, AND METHODS FOR TREATING OF INTRACRANIAL ANEURYSMS; and International Application No. PCT/US2020/070742, filed concurrently herewith, titled SYSTEMS AND METHODS FOR TREATING ANEURYSMS.

TECHNICAL FIELD

The present technology relates to systems, devices, and methods for treating intracranial aneurysms.

BACKGROUND

An intracranial aneurysm is a portion of an intracranial blood vessel that bulges outward from the blood vessel's main channel. This condition often occurs at a portion of a blood vessel that is abnormally weak because of a congenital anomaly, trauma, high blood pressure, or for another reason. Once an intracranial aneurysm forms, there is a significant risk that the aneurysm will eventually rupture and cause a medical emergency with a high risk of mortality due to hemorrhaging. When an unruptured intracranial aneurysm is detected or when a patient survives an initial rupture of an intracranial aneurysm, vascular surgery is often indicated.

One conventional type of vascular surgery for treating an intracranial aneurysm includes using a microcatheter to dispose a platinum coil within an interior volume of the aneurysm. Over time, the presence of the coil should induce formation of a thrombus. Ideally, the aneurysm's neck closes at the site of the thrombus and is replaced with new endothelial tissue. Blood then bypasses the aneurysm, thereby reducing the risk of aneurysm rupture (or re-rupture) and associated hemorrhaging. Unfortunately, long-term recanalization (i.e., restoration of blood flow to the interior volume of the aneurysm) after this type of vascular surgery occurs in a number of cases, especially for intracranial aneurysms with relatively wide necks and/or relatively large interior volumes.

Another conventional type of vascular surgery for treating an intracranial aneurysm includes deploying a flow diverter within the associated intracranial blood vessel. The flow diverter is often a mesh tube that causes blood to preferentially flow along a main channel of the blood vessel while blood within the aneurysm stagnates. The stagnant blood within the aneurysm should eventually form a thrombus that leads to closure of the aneurysm's neck and to growth of new endothelial tissue, as with the platinum coil treatment. One significant drawback of flow diverters is that it may take weeks or months to form aneurysmal thrombus and significantly longer for the aneurysm neck to be covered with endothelial cells for full effect. This delay may be unacceptable when risk of aneurysm rupture (or re-rupture) is high. Moreover, flow diverters typically require antiplatelet therapy to prevent a thrombus from forming within the main channel of the blood vessel at the site of the flow diverter. Antiplatelet therapy may be contraindicated shortly after an initial aneurysm rupture has occurred because risk of re-rupture at this time is high and antiplatelet therapy tends to exacerbate intracranial hemorrhaging if re-rupture occurs. For these and other reasons, there is a need for innovation in the treatment of intracranial aneurysms. Given the severity of this condition, innovation in this field has immediate life-saving potential.

SUMMARY

The present technology is illustrated, for example, according to various aspects described below. Various examples of aspects of the present technology are described as numbered clauses (1, 2, 3, etc.) for convenience. These are provided as examples and do not limit the present technology. It is noted that any of the dependent clauses may be combined in any combination, and placed into a respective independent clause. The other clauses can be presented in a similar manner.

1. A treatment system comprising:
    an occlusive member configured to be positioned within an aneurysm sac, the occlusive member comprising a hub;
    an elongate tubular member having an engagement member removably coupled to the hub, the elongate tubular member defining a first lumen extending therethrough; and
    a conduit extending within the first lumen, the conduit defining a second lumen configured to receive an embolic element therethrough.
2. The treatment system of any one of the previous Clauses, wherein the engagement member is removably coupled to the hub via an interference fit.

3. The treatment system of any one of the previous Clauses, wherein the hub has a recess, and the engagement member comprises a protrusion configured to be removably received within the recess.

4. The treatment system of any one of the previous Clauses, wherein the elongate tubular member comprises a hypotube.

5. The treatment system of any one of the previous Clauses, further comprising a control element configured to extend within the first lumen.

6. The treatment system of any one of the previous Clauses, wherein the control element urges the engagement member into engagement with the hub.

7. The treatment system of any one of the previous Clauses, wherein the control element comprises a wire or rod.

8. The treatment system of any one of the previous Clauses, wherein the control element restrains or inhibits the engagement member from decoupling from the hub.

9. The treatment system of any one of the previous Clauses, wherein the control element is slidably removable from the first lumen.

10. The treatment system of any one of the previous Clauses, wherein the control element extends within the second lumen.

11. The treatment system of any one of the previous Clauses, wherein the control element extends outside the second lumen, alongside the conduit.

12. The treatment system of any one of the previous Clauses, wherein the conduit comprises a flexible tubular member.

13. The treatment system of any one of the previous Clauses, further comprising a restraint disposed radially adjacent the engagement member.

14. The treatment system of any one of the previous Clauses, wherein the restraint comprises an expandable element configured to exert a radially outward force on the engagement member.

15. The treatment system of any one of the previous Clauses, wherein the restraint is coupled to a pull wire such that the restraint can be slidably retracted and/or is movable relative to the engagement member.

16. The treatment system of any one of the previous Clauses, wherein the restraint is disposed within second lumen.

17. The treatment system of any one of the previous Clauses, wherein the restraint is incorporated within a wall of the conduit.

18. The delivery system of any one of the previous Clauses, wherein the restraint comprises a reinforced portion of the conduit.

19. A treatment system comprising:
an occlusive member configured to be positioned at a treatment site, the occlusive member comprising a hub;
a conduit having an engagement portion removably threadably engaged with the hub; and
a lumen extending through the conduit and configured to convey an embolic element therethrough to the treatment site.

20. The treatment system of any one of the previous Clauses, wherein the hub comprises radially inwardly facing threads, and wherein the engagement portion comprises corresponding radially outwardly facing threads.

21. The treatment system of any one of the previous Clauses, wherein the conduit can be rotatably engaged or disengaged from the hub.

22. The treatment system of any one of the previous Clauses, wherein the conduit can be engaged or disengaged from the hub by rotation of the conduit.

23. The treatment system of any one of the previous Clauses, wherein the embolic element is configured to be delivered distal to the occlusive member.

24. The treatment system of any one of the previous Clauses, wherein the conduit comprises a hypotube or catheter.

25. The treatment system of any one of the previous Clauses, wherein the conduit, when threadably engaged with the hub, comprises a proximal portion extending proximally from the hub and a distal portion extending distally from the hub.

26. The treatment system of any one of the previous Clauses, wherein the distal portion of the conduit extends distally beyond the occlusive member in its expanded state.

27. A treatment system comprising:
an occlusive member configured to be positioned within an aneurysm;
a distal conduit coupled to the occlusive member and defining a first lumen;
a proximal conduit having an engagement portion threadably engaged with the occlusive member, the proximal conduit defining a second lumen therethrough and configured such that, when the proximal conduit is threadably engaged with the occlusive member, the first lumen and the second lumen are in fluid communication and are configured to convey an embolic element therethrough.

28. The treatment system of any one of the previous Clauses, wherein the occlusive member comprises a hub having radially inwardly facing threads, and wherein the engagement portion comprises corresponding radially outwardly facing threads.

29. The treatment system of any one of the previous Clauses, wherein the distal conduit comprises radially inwardly facing threads, and wherein the engagement portion comprises corresponding radially outwardly facing threads.

30. The treatment system of any one of the previous clauses, wherein the proximal conduit can be engaged or disengaged from the occlusive member by rotation of the proximal conduit.

31. The treatment system of any one of the previous Clauses, wherein the embolic element is configured to be delivered via the distal conduit at a location distal to the occlusive member in its expanded state.

32. The treatment system of any one of the previous Clauses, wherein the proximal conduit comprises a hypotube or catheter.

33. The treatment system of any one of the previous Clauses, wherein the proximal conduit, when threadably engaged with the hub, comprises a proximal portion extending proximally from the hub and a distal portion extending distally from the hub.

34. The treatment system of any one of the previous Clauses, wherein the occlusive member comprises an expandable mesh having a constrained state for delivery to an aneurysm and an expanded state in which at least a portion of the mesh is configured to be disposed across a neck of the aneurysm.

35. The treatment system of any one of the previous Clauses, wherein the expandable mesh comprises a plurality of braided filaments that assume a pre-set, three-dimensional shape in the expanded state.

36. The treatment system of any one of the previous Clauses, wherein the expandable mesh comprises a braid formed of 24, 32, 36, 48, 64, or 72 filaments.

37. The treatment system of any one of the previous Clauses, wherein the expandable mesh comprises a braid formed of a plurality of wires, some or all of which have a diameter of at least 0.001 inches.

38. The treatment system of any one of the previous Clauses, wherein the expandable mesh comprises a braid formed of a plurality of wires, some or all of which have the same diameter.

39. The treatment system of any one of the previous Clauses, wherein the expandable mesh comprises a braid formed of a plurality of wires, at least some of which have different diameters.

40. The treatment system of any one of the previous Clauses, wherein, in the expanded state, the expandable mesh forms one of a sphere, a prolate spheroid, or an oblate spheroid.

41. The treatment system of any one of the previous Clauses, wherein the expandable mesh comprises an inner layer and an outer layer.

42. The treatment system of any one of the previous Clauses, wherein the expandable mesh has a maximum cross-sectional dimension of 3.0 mm, 3.5 mm, 4.0 mm, 4.5 mm, 5.0 mm, 5.5 mm, 6.0 mm, 6.5 mm, 7.0 mm, 7.5 mm, or 8.0 mm.

43. The treatment system of any one of the previous Clauses, wherein the expandable mesh is a laser-cut tube.

44. The treatment system of any one of the previous Clauses, wherein the expandable mesh comprises a plurality of interwoven filaments.

45. The treatment system of any one of the previous Clauses, wherein the occlusive member is curved along at least a majority of its entire length.

46. The treatment system of any one of the previous Clauses, wherein the occlusive member is collapsible when contacted by a synthetic gel or fluid.

47. The treatment system of any one of the previous Clauses, wherein the occlusive member is configured to rotate about the conduit.

48. The treatment system of any one of the previous Clauses, wherein the occlusive member is rotatably and slidably coupled to the conduit.

49. The treatment system of any one of the previous Clauses, wherein the occlusive member has an aperture at a distal portion thereof, and wherein the elongate tubular member extends through the aperture.

50. The treatment system of any one of the previous Clauses, wherein the occlusive member is configured to move axially along the elongate tubular member.

51. The treatment system of any one of the previous Clauses, wherein the embolic element is a liquid embolic.

52. The treatment system of any one of the previous Clauses, wherein the embolic element comprises a biopolymer and/or a chemical crosslinking agent.

53. The treatment system of any one of the previous Clauses, wherein the biopolymer includes chitosan, a derivative of chitosan, an analog of chitosan, or a combination thereof.

54. The treatment system of any one of the previous Clauses, wherein the chemical crosslinking agent includes genipin, a derivative of genipin, an analog of genipin, or a combination thereof.

55. A system comprising:
the treatment system of any one of the previous Clauses; and
an elongate shaft having a lumen extending therethrough, wherein the treatment system is configured to be slidably disposed within the lumen of the elongate shaft.

56. A system comprising:
the treatment system of any one of the previous Clauses;
a first elongate shaft having a first lumen extending therethrough, wherein the treatment system is configured to be slidably disposed within the first lumen; and
a second elongate shaft having a second lumen extending therethrough, wherein the first elongate shaft is configured to be slidably disposed within the second lumen.

57. The treatment system of one of the previous Clauses, wherein the first elongate shaft is a microcatheter and the second elongate shaft is a delivery or guide catheter.

58. A method for treating an aneurysm, comprising:
providing the treatment system of any one of the previous Clauses.

59. The method of one of the previous Clauses, further comprising:
positioning a distal end of the conduit of the treatment system in an aneurysm cavity; and releasing the occlusive member of the treatment system from the conduit while the distal end of the conduit is positioned within the aneurysm cavity such that the occlusive member self-expands to assume an expanded state.

60. The method of any one of the previous Clauses, further comprising delivering an embolic element through the distal end of the distal conduit to the treatment site.

61. The method of any one of the previous Clauses, wherein releasing the occlusive member comprises retracting the control element with respect to the engagement member.

62. The method of any one of the previous Clauses, wherein releasing the occlusive member comprises deflecting the engagement member away from the hub.

63. The method of any one of the previous Clauses, wherein releasing the occlusive member comprises retracting the engagement member with respect to the hub.

64. The method of any one of the previous Clauses, wherein releasing the occlusive member comprises retracting the restraint with respect to the engagement member, and then retracting the engagement member with respect to the hub.

65. The method of any one of the previous Clauses, wherein releasing the occlusive member comprises rotating the conduit with respect to the hub or occlusive member.

66. The method of any one of the previous Clauses, further comprising proximally retracting the proximal conduit while the occlusive member remains in place at the treatment site.

67. The method of any one of the previous Clauses, wherein releasing the occlusive member comprises allowing the occlusive member to self-expand to assume a first expanded state in which the occlusive member forms a first shape, wherein, in the first expanded state, the occlusive member encloses an interior region having a first interior volume, the method further comprising delivering an embolic element between the occlusive member and the aneurysm wall to transform the occlusive member into a second expanded state in which the occlusive member defines a second interior volume less than the first interior volume, wherein the occlusive member forms a second shape in the second expanded state that is different than the first shape in the first expanded state.

68. The method of any one of the previous Clauses, wherein transforming the occlusive member into the second expanded shape includes injecting the embolic material to urge a portion of a sidewall of the expandable mesh in a direction away from a wall of the aneurysm and towards the interior region of the occlusive member.

69. The method of any one of the previous Clauses, wherein transforming the occlusive member into the second expanded shape includes injecting the embolic material to invert a portion of a sidewall of the occlusive member such that the portion is convex towards the aneurysm wall in the first expanded state and concave towards the aneurysm wall in the second expanded state.

70. The method of any one of the previous Clauses, wherein the embolic element comprises a liquid embolic.

71. The method of any one of the previous Clauses, wherein the embolic element comprises one or more embolization coils.

72. The method of any one of the previous Clauses, wherein delivering the embolic element occurs after the occlusive member is in the first expanded state.

73. The method of any one of the previous Clauses, wherein the occlusive member is a mesh.

74. The method of any one of the previous Clauses, wherein the occlusive member is a braid.

75. The method of any one of the previous Clauses, wherein the occlusive member is a dual-layered braid.

76. The method of any one of the previous Clauses, wherein the occlusive member has a globular or generally spherical shape in the first expanded state.

77. The method of any one of the previous Clauses, wherein the occlusive member is cup or bowl-shaped in the second expanded state.

78. The method of any one of the previous Clauses, wherein the second shape is a predetermined three-dimensional shape.

79. The method of any one of the preceding Clauses, wherein the occlusive member forms a multi-layer braid at the neck of the aneurysm in the second expanded state.

80. The method of any one of the previous Clauses, wherein the occlusive member comprises a plurality of braided filaments that assume a pre-set, three-dimensional shape in the expanded state.

81. The method of any one of the previous Clauses, wherein the occlusive member comprises a braid formed of 24, 32, 36, 48, 64, or 72 filaments.

82. The method of any one of the previous Clauses, wherein the occlusive member comprises a braid formed of a plurality of wires, some or all of which have a diameter of about 0.001 inches (0.00254 cm).

83. The method of any one of the previous Clauses, wherein the occlusive member comprises a braid formed of a plurality of wires, some or all of which have the same diameter.

84. The method of any one of the previous Clauses, wherein the occlusive member comprises a braid formed of a plurality of wires, at least some of which have different diameters.

85. The method of any one of the previous Clauses, wherein the occlusive member forms a closed, globular shape in the expanded state, the mesh having an aperture at a distal portion.

86. The method of any one of the previous Clauses, wherein, in the expanded state, the occlusive member forms one of a sphere, a prolate spheroid, or an oblate spheroid.

87. The method of any one of the previous Clauses, wherein the occlusive member comprises an inner layer and an outer layer.

88. The method of any one of the previous Clauses, wherein the occlusive member comprises an inner layer and an outer layer that meet at a fold at a distal portion of the occlusive member.

89. The method of any one of the previous Clauses, wherein the expandable mesh includes an aperture at a distal portion, the aperture being defined by the fold.

90. The method of any one of the previous Clauses, wherein the occlusive member comprises an inner layer and an outer layer that meet at a fold at a proximal portion of the occlusive member.

91. The method of any one of the previous Clauses, wherein the expandable mesh includes an aperture at a distal portion, the aperture being defined by the fold.

92. The method of any one of the previous Clauses, wherein the occlusive member has a maximum cross-sectional dimension of 3.0 mm, 3.5 mm, 4.0 mm, 4.5 mm, 5.0 mm, 5.5 mm, 6.0 mm, 6.5 mm, 7.0 mm, 7.5 mm, or 8.0 mm.

93. The method of any one of the previous Clauses, wherein the occlusive member is formed of a plurality of filaments having first and second ends fixed at the hub or a coupler.

94. The method of any one of the previous Clauses, wherein the occlusive member is formed of a plurality of filaments formed of an inner core material surrounded by an outer material.

95. The method of any one of the previous Clauses, wherein the inner core material is a radiopaque material and the outer material is a superelastic material.

96. The method of any one of the previous Clauses, wherein the occlusive member is a laser-cut tube.

97. The method of any one of the previous Clauses, wherein the occlusive member comprises a plurality of filaments.

98. The method of any one of the previous Clauses, wherein the filaments are interwoven.

99. The method of any one of the previous Clauses, wherein the filaments are braided.

100. The method of any one of the previous Clauses, wherein each of the filaments has a first end and a second end opposite the first end, and wherein both the first and second ends of the filaments are fixed relative to one another at a coupler.

101. The method of any one of the previous Clauses, wherein the coupler is disposed at a distal end of the occlusive member.

102. The method of any one of the previous Clauses, wherein the coupler is disposed at a proximal end of the occlusive member.

103. The method of any one of the previous Clauses, wherein each of the filaments terminate at only one end of the distal element.

104. The method of any one of the previous Clauses, wherein the filaments form an opening at an end of the distal element opposite the only one end.

105. The method of any one of the previous Clauses, wherein an inverted portion of each of the filaments define the opening.

106. The method of any one of the previous Clauses, wherein the inverted portions of the filaments are configured to move relative to one another.

107. The method of any one of the previous Clauses, wherein the embolic element comprises a biopolymer and a chemical crosslinking agent.

108. The method of any one of the previous Clauses, wherein the biopolymer includes chitosan, a derivative of chitosan, an analog of chitosan, or a combination thereof.

109. The method of any one of the previous Clauses, wherein the chemical crosslinking agent includes genipin, a derivative of genipin, an analog of genipin, or a combination thereof.

110. The method of any one of the previous Clauses, wherein the embolic element further comprises a physical crosslinking agent.

111. The method of any one of the previous Clauses, the physical crosslinking agent includes β glycerophosphate, a derivative of β glycerophosphate, an analog of β glycerophosphate, or a combination thereof.

112. The method of any one of the previous Clauses, wherein
 the biopolymer includes chitosan, a derivative of chitosan, an analog of chitosan, or a combination thereof;
 the chemical crosslinking agent includes genipin, a derivative of genipin, an analog of genipin, or a combination thereof; and
 the physical crosslinking agent includes β glycerophosphate, a derivative of β glycerophosphate, an analog of β glycerophosphate, or a combination thereof.

113. The method of any one of the previous Clauses, wherein the embolic element comprises a contrast agent.

114. The method of any one of the previous Clauses, wherein the contrast agent is selected to provide diminishing radiopacity.

115. The method of any one of the previous Clauses, wherein the contrast agent includes iohexol, a derivative of iohexol, an analog of iohexol, or a combination thereof.

Additional features and advantages of the present technology are described below, and in part will be apparent from the description, or may be learned by practice of the present technology. The advantages of the present technology will be realized and attained by the structure particularly pointed out in the written description and claims hereof as well as the appended drawings.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present disclosure.

FIG. 1A shows a perspective view of a system for treating an aneurysm in accordance with the present technology.

DETAILED DESCRIPTION

Figure 1B:
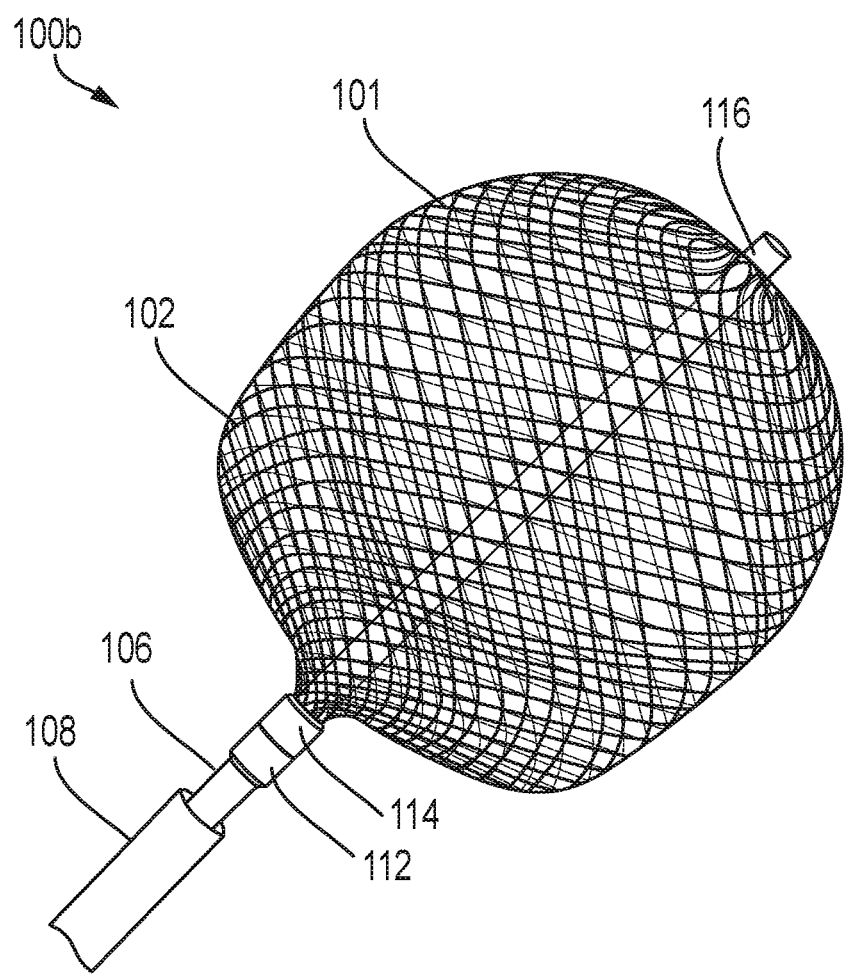
FIG. 1B shows an enlarged view of a distal portion of the treatment system of FIG. 1A in accordance with the present technology.

Methods for treating intracranial aneurysms in accordance with at least some embodiments of the present technology include positioning an expandable occlusive member within the aneurysm and introducing an embolic element between the occlusive member and an aneurysm wall. Introduction of the embolic element both fills space within the aneurysm cavity and deforms the occlusive member from a first expanded state to a second expanded state to fortify the occlusive member at the neck of the aneurysm. Deformation of the occlusive member from a first expanded state to a second expanded state provides the additional advantage of giving visual confirmation to the physician that the delivered amount of embolic element sufficiently fills the aneurysm cavity. In addition to providing a structural support and anchor for the embolic element, the occlusive member provides a scaffold for tissue remodeling and diverts blood flow from the aneurysm. Moreover, the embolic element exerts a substantially uniform pressure on the occlusive member towards the neck of the aneurysm, thereby pressing the portions of the occlusive member positioned adjacent the neck against the inner surface of the aneurysm wall such that the occlusive member forms a complete and stable seal at the neck.

Once the occlusive member has deployed within the aneurysm and the embolic element has been delivered, the occlusive member may be detached from the delivery assembly. Suitable detachment mechanisms must be as small as possible so as to be guided through the fine bore of the catheter to the treatment site, while on the other hand they must securely and reliably produce detachment of the intrasaccular implant. Absent a reliable detachment of the intrasaccular implant, withdrawal of the delivery wire and catheter may cause unintended removal of the occlusive member from the cavity to be occluded and thus injure and/or rupture of the wall of the cavity or vessel. In some embodiments, a detachment mechanism employing an interference fit, threadable engagement, or other mechanical detachment mechanism as described herein can be used to facilitate reliable, controlled detachment of the occlusive member.

Specific details of systems, devices, and methods for treating intracranial aneurysms in accordance with embodiments of the present technology are described herein with reference to FIGS. 1A-9B. Although these systems, devices, and methods may be described herein primarily or entirely in the context of treating saccular intracranial aneurysms, other contexts are within the scope of the present technology. For example, suitable features of described systems, devices, and methods for treating saccular intracranial aneurysms can be implemented in the context of treating nonsaccular intracranial aneurysms, abdominal aortic aneurysms, thoracic aortic aneurysms, renal artery aneurysms, arteriovenous malformations, tumors (e.g. via occlusion of vessel(s) feeding a tumor), perivascular leaks, varicose veins (e.g. via occlusion of one or more truncal veins such as the great saphenous vein), hemorrhoids, and sealing endoleaks adjacent to artificial heart valves, covered stents, and abdominal aortic aneurysm devices among other examples. Furthermore, it should be understood, in general, that other systems, devices, and methods in addition to those disclosed herein are within the scope of the present disclosure. For example, systems, devices, and methods in accordance with embodiments of the present technology can have different and/or additional configurations, components, procedures, etc. than those disclosed herein. Moreover, systems, devices, and methods in accordance with embodiments of the present disclosure can be without one or more of the configurations, components, procedures, etc. disclosed herein without deviating from the present technology.

I. Overview of Systems of the Present Technology

FIG. 1A illustrates a view of a system 10 for treating intracranial aneurysms according to one or more embodiments of the present technology. As shown in FIG. 1A, the system 10 comprises a treatment system 100 and an embolic kit 200 for use with one or more components of the treatment system 100. The treatment system 100 may comprise an occlusive member 102 (shown in an expanded state) detachably coupled to a delivery system, and the delivery system may be configured to intravascularly position the occlusive member 102 within an aneurysm. The embolic kit 200 may comprise one or more substances or devices that alone or in combination form an embolic element that is configured to co-occupy the internal volume of the aneurysm with the occlusive member 102. In some embodiments, the treatment system 100 may be configured to deliver the embolic element (and/or one or more precursors thereof) to the aneurysm. Additionally or alternatively, the system 10 may include a separate delivery system (not shown) for delivering the embolic element (and/or one or more precursors thereof) to the aneurysm cavity.

As shown in FIG. 1A, the treatment system 100 has a proximal portion 100a configured to be extracorporeally positioned during treatment and a distal portion 100b configured to be intravascularly positioned within a blood vessel (such as an intracranial blood vessel) at a treatment site at or proximate an aneurysm. The treatment system 100 may include a handle 103 at the proximal portion 100a, the occlusive member 102 at the distal portion 100b, and a plurality of elongated shafts or members extending between the proximal and distal portions 100a and 100b. In some embodiments, such as that shown in FIG. 1A, the treatment system 100 may include a first elongated shaft 109 (such as a guide catheter or balloon guide catheter), a second elongated shaft 108 (such as a microcatheter) configured to be slidably disposed within a lumen of the first elongated shaft 109, and an elongated member 106 configured to be slidably disposed within a lumen of the second elongated shaft 108. In some embodiments, the treatment system 100 does not include the first elongated shaft 109 and only includes the second elongated shaft 108.

FIG. 1B is an enlarged view of the distal portion 100b of the treatment system 100. Referring to FIGS. 1A and 1B together, the occlusive member 102 may be detachably coupled to a distal end of the elongate tubular member 106. For example, the elongated member 106 may include a first coupler 112 at its distal end, and the occlusive member 102 may include a second coupler 114 configured to detachably couple with the first coupler 112. In some embodiments, the first and second couplers 112, 114 can take the form of an interference-fit mechanical detachment mechanism (as described in more detail below with respect to FIGS. 4A-8) or a threadable mechanical detachment mechanism (as described in more detail below with respect to FIGS. 9A-10B). The treatment system 100 may further comprise a conduit 116 extending from the handle 103 (for example, via port 110) distally to the distal portion 100b of the treatment system 100. The conduit 116 is configured to deliver the embolic element (and/or one or more precursors thereof) through one or more components of the delivery system (e.g., the first or second elongate shafts 109, 108, the elongated member 106, etc.) to a position at the exterior of the occlusive member 102. As such, the embolic element may be positioned between the occlusive member 102 and an inner wall of the aneurysm cavity, as described in greater detail below.

According to some embodiments, the second elongate shaft 108 is generally constructed to track over a conventional guidewire in the cervical anatomy and into the cerebral vessels associated with the brain and may also be chosen according to several standard designs that are generally available. Accordingly, the second elongate shaft 108 can have a length that is at least 125 cm long, and more particularly may be between about 125 cm and about 175 cm long. In some embodiments, the second elongate shaft 108 may have an inner diameter of about 0.015 inches (0.0381 cm), 0.017 inches (0.043 cm), about 0.021 inches (0.053 cm), or about 0.027 inches (0.069 cm). Other designs and dimensions are contemplated.

The elongated member 106 can be movable within the first and/or second elongate shafts 109, 108 to position the occlusive member 102 at a desired location. The elongated member 106 can be sufficiently flexible to allow manipulation, e.g., advancement and/or retraction, of the occlusive member 102 through tortuous passages. Tortuous passages can include, for example, catheter lumens, microcatheter lumens, blood vessels, urinary tracts, biliary tracts, and airways. The elongated member 106 can be formed of any material and in any dimensions suitable for the task(s) for which the system is to be employed. In some embodiments, the elongated member 106 can comprise a solid metal wire. In some embodiments, the elongated member 106 may comprise any other suitable form of shaft such as an elongate tubular shaft.

In some embodiments, the elongated member 106 can comprise stainless steel, nitinol, or other metal or alloy. In some embodiments, the elongated member 106 can be surrounded over some or all of its length by a coating, such as, for example, polytetrafluoroethylene. The elongated member 106 may have a diameter that is generally constant along its length, or the elongated member 106 may have a diameter that tapers radially inwardly, along at least a portion of its length, as it extends in a distal direction.

According to several embodiments, the conduit 116 may be a catheter or elongated shaft that is delivered separately from the second elongated shaft 108.

A. Selected Examples of Occlusive Members

Figure 1C:
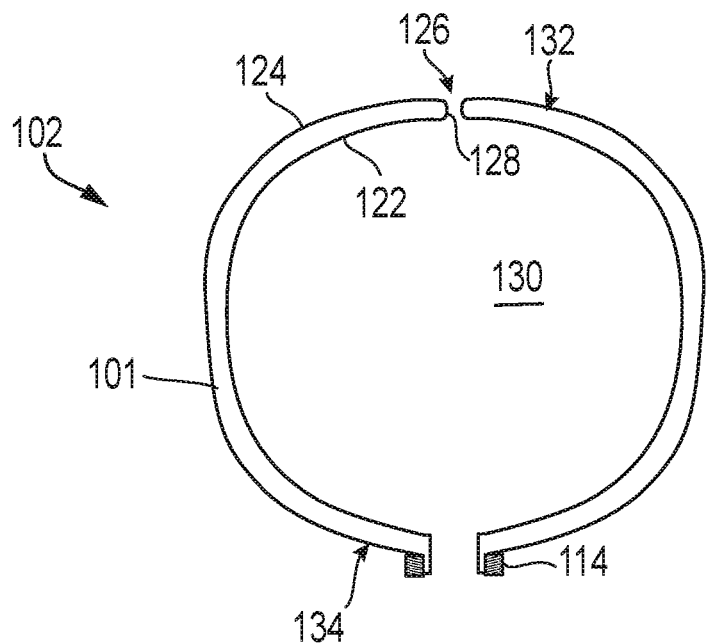
FIGS. 1C and 1D are sectioned views of occlusive members in an expanded state in accordance with the present technology.

FIG. 1C is a sectioned view of the occlusive member 102, shown in an expanded state and detached from the treatment system 100. Referring to FIGS. 1B and 1C, the occlusive member 102 may comprise an expandable element having a low-profile or constrained state while positioned within a catheter (such as the second elongated shaft 108) for delivery to the aneurysm and an expanded state in which the expandable element is configured to be positioned within an aneurysm (such as a cerebral aneurysm).

According to some embodiments, the occlusive member 102 may comprise a mesh 101 formed of a plurality of braided filaments that have been heat-set to assume a predetermined shape enclosing an interior volume 130 when the mesh 101 is in an expanded, unconstrained state. Example shapes include a globular shape, such as a sphere, a prolate spheroid, an oblate spheroid, and others. As depicted in FIG. 1C, the mesh 101 may have inner and outer layers 122, 124 that have proximal ends fixed relative to one another at the second coupler 114 and meet distally at a distal fold 128 surrounding an aperture 126. While the inner and outer layers 122, 124 are depicted spaced apart from one another along their lengths, the inner and outer layers 122, 124 may be in contact with one another along all or a portion of their lengths. For example, the inner layer 122 may press radially outwardly against the outer layer 124. In some embodiments, the occlusive member 102 may be formed of a single layer or mesh or braid.

In some embodiments, the inner and outer layers 122, 124 have their distal ends fixed relative to one another at a distal coupler and meet proximally at a proximal fold surrounding an aperture. In any case, in some embodiments the conduit 116 may be configured to be slidably positioned through some or all of the second coupler 114, the interior volume 130 of the expanded mesh 101, and the opening 126.

The inner and outer layers 122 and 124 may conform to one another at the distal portion (for example as shown in FIG. 1C) to form a curved distal surface. For example, at least at the distal portion of the occlusive member 102, the inner and outer layers 122 and 124 may extend distally and radially inwardly, towards the aperture 126. In some embodiments, the outer and/or inner layers 122 and 124 extend distally and radially outwardly from the second coupler 114, then extend distally and radially inwardly up to a distal terminus of the occlusive member 102 (e.g., the fold 128). The occlusive member 102 and/or layers thereof may be curved along its entire length, or may have one or more generally straight portions. In some embodiments, the curved surface transitions to a flat or substantially flat, distal-most surface that surrounds the aperture 126. In some embodiments, the curved surface transitions to a distal-most surface that surrounds the aperture 126 and has a radius of curvature that is greater than the average radius of curvature of the rest of the occlusive member 102. Having a flat or substantially flat distal surface, or a distal surface with a radius of curvature that is greater than the average radius of curvature of the rest of the occlusive member 102, may be beneficial for delivering the embolic element 230 in that it creates a small gap between the distal surface of the occlusive member 102 and the dome of the aneurysm A (see, for example, FIG. 3B). In some embodiments, the surface of the occlusive member 102 surrounding the aperture 126 is curved and/or has generally the same radius of curvature as the remainder of the occlusive member 102.

Figure 1D:
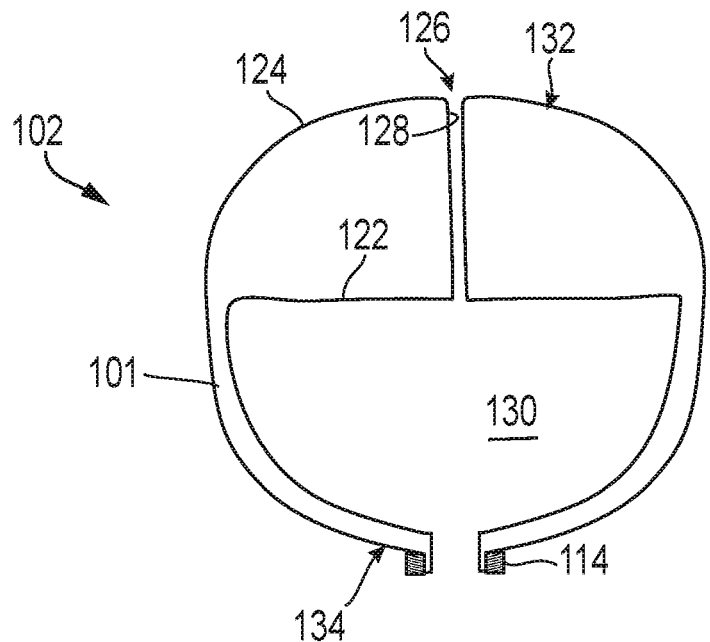
Figure 2:
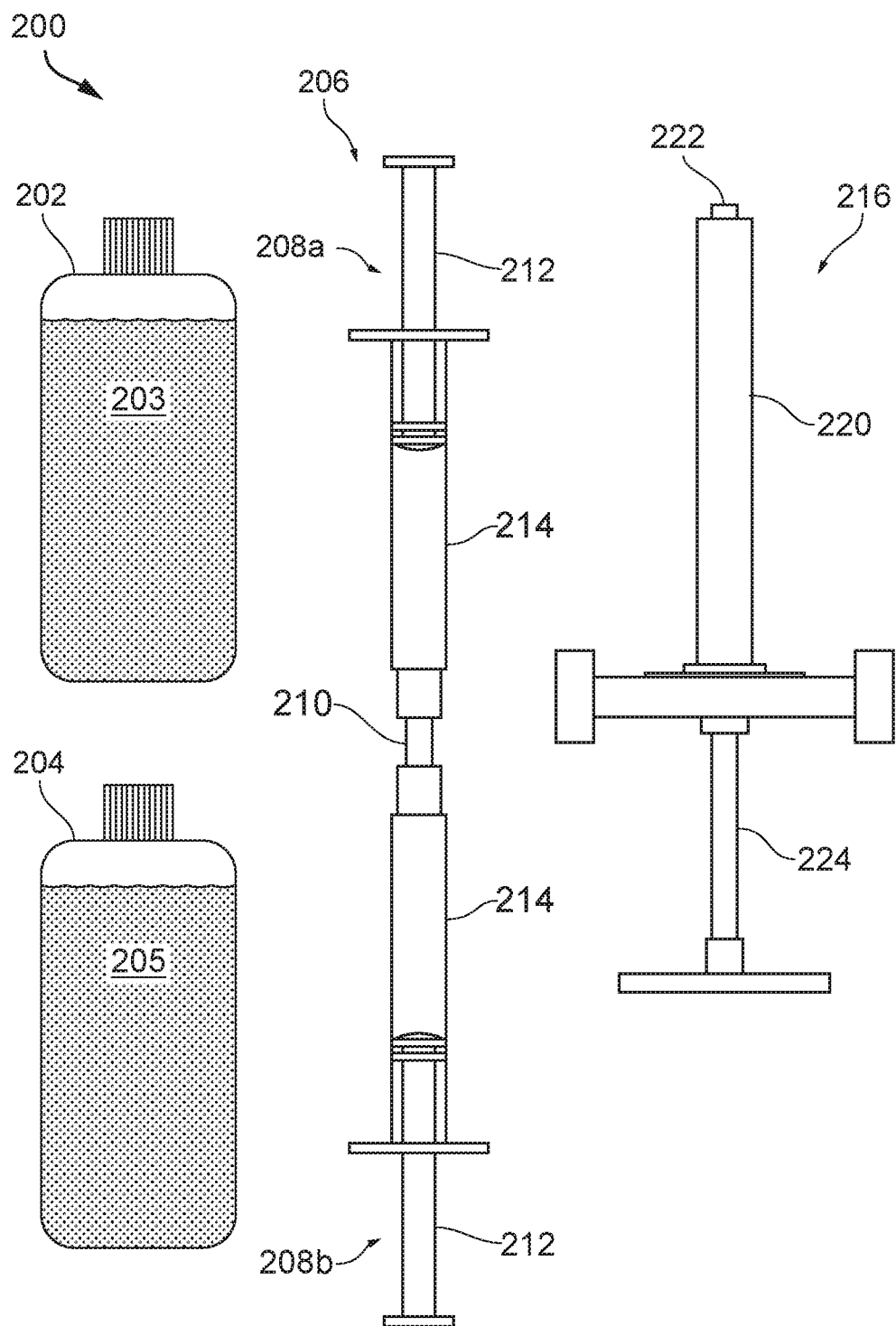
FIG. 2 shows an embolic kit according to the present technology.

In any case, the inner layer 124 may have a shape that substantially conforms to the shape of the outer layer 124, or the inner and outer layers 122, 124 may have different shapes. For example, as shown in FIG. 1D, the inner layer 122 may have a diameter or cross-sectional dimension that is less than the outer layer 124. Such a configuration may be beneficial in that the embolic element 230 experiences less resistance, at least initially, when pushing the distal wall of the occlusive member 102 downwardly towards the neck (as described in greater detail below).

In any case, both the proximal portion and the distal portion of the mesh 101 can form generally closed surfaces. However, unlike at the proximal portion of the mesh 101, the portion of the filaments at or near the fold 128 at the distal portion of the mesh 101 can move relative to one another. As such, the distal portion of the mesh 101 has both the properties of a closed end and also some properties of an open end (like a traditional stent), such as some freedom of movement of the distal-most portions of the filaments and an opening through which the conduit 116, a guidewire, guidetube, or other elongated member may pass through.

In some embodiments, each of the plurality of filaments have a first end positioned at the proximal portion of the mesh 101 and a second end also positioned at the proximal portion of the mesh 101. Each of the filaments may extend from its corresponding first end distally along the body of the mesh 101 to the fold 128, invert, then extend proximally along the mesh body to its corresponding second end at the proximal portion of the mesh 101. As such, each of the plurality of filaments have a first length that forms the inner layer 122 of the mesh 101, a second length that forms the outer layer 124 of the mesh 101, and both first and second ends fixed at the proximal portion of the mesh 101. In some embodiments, the occlusive member 102 may comprise a mesh formed of a single layer, or a mesh formed of three or more layers.

In some embodiments, the distal end surface of the mesh 101 is completely closed (i.e., does not include an aperture). In some embodiments the filaments are fixed relative to the at both the proximal and distal ends of the occlusive member 102.

The mesh 101 may be formed of metal wires, polymer wires, or both, and the wires may have shape memory and/or superelastic properties. The mesh 101 may be formed of 24, 32, 36, 48, 64, 72, 96, 128, or 144 filaments. The mesh 101 may be formed of a range of filament or wire sizes, such as wires having a diameter of from about 0.0004 inches to about 0.0020 inches, or of from about 0.0009 inches to about 0.0012 inches. In some embodiments, each of the wires or filaments have a diameter of about 0.0004 inches, about 0.0005 inches, about 0.0006 inches, about 0.0007 inches, about 0.0008 inches, about 0.0009 inches, about 0.001 inches, about 0.0011 inches, about 0.0012 inches, about 0.0013 inches, about 0.0014 inches, about 0.0015 inches, about 0.0016 inches, about 0.0017 inches, about 0.0018 inches, about 0.0019 inches, or about 0.0020 inches. In some embodiments, all of the filaments of the braided mesh 101 may have the same diameter. For example, in some embodiments, all of the filaments have a diameter of about 0.001 inches. In some embodiments, some of the filaments may have different cross-sectional diameters. For example, some of the filaments may have a slightly thicker diameter to impart additional strength to the braided layers. In some embodiments, some of the filaments can have a diameter of about 0.001 inches, and some of the filaments can have a diameter of greater than 0.001 inches. The thicker filaments may impart greater strength to the braid without significantly increasing the device delivery profile, with the thinner wires offering some strength while filling-out the braid matrix density.

The occlusive member 102 can have different shapes and sizes in an expanded, unconstrained state. For example, the occlusive member 102 may have a bullet shape, a barrel-shape, an egg shape, a dreidel shape, a bowl shape, a disc shape, a cylindrical or substantially cylindrical shape, a barrel shape, a chalice shape, etc.

B. Selected Examples of Embolic Kits

The embolic kit 200 may include one or more precursors for creation of a liquid embolic. For example, the embolic kit 200 may include a first container 202 containing a first precursor material 203 (shown schematically), a second container 204 containing a second precursor material 205 (also shown schematically), and a mixing device 206 suitable for mixing the first and second precursor materials 203, 205. The mixing device 206 can include mixing syringes 208 (individually identified as mixing syringes 208a, 208b) and a coupler 210 extending between respective exit ports (not shown) of the mixing syringes 208. The mixing syringes 208a, 208b each include a plunger 212 and a barrel 214 in which the plunger 212 is slidably received.

The embolic kit 200 can further include an injection syringe 216 configured to receive a mixture of the first and second precursor materials 203, 205 and deliver the mixture to a proximal portion 100b of the treatment assembly 100. The injection syringe 216 can include a barrel 220, an exit port 222 at one end of the barrel 220, and a plunger 224 slidably received within the barrel 220 via an opposite end of the barrel 220. The handle 103 of the treatment system 100 may have a coupler configured to form a secure fluidic connection between the lumen and the exit port 222 of the injection syringe 216.

The first and second precursor materials 203, 205 can include a biopolymer and a chemical crosslinking agent, respectively. The chemical crosslinking agent can be selected to form covalent crosslinks between chains of the biopolymer. In some embodiments, the biopolymer of the first precursor material 203 includes chitosan or a derivative or analog thereof, and the chemical crosslinking agent of the second precursor material 205 includes genipin or a derivative or analog thereof. Other suitable crosslinking agents for use with chitosan include glutaraldehyde, functionalized polyethylene glycol, and derivatives and analogs thereof. In other embodiments, the biopolymer of the first precursor material 203 can include collagen or a derivative or analog thereof, and the chemical crosslinking agent of the second precursor material 205 can include hexamethylene diisocyanate or a derivative or analog thereof. Alternatively or in addition, genipin or a derivative or analog thereof can be used as a chemical crosslinking agent for a collagen-based biopolymer. In still other embodiments, the biopolymer of the first precursor material 203 and the chemical crosslinking agent of the second precursor material 205 can include other suitable compounds alone or in combination.

Mixing the biopolymer of the first precursor material 203 and the chemical crosslinking agent of the second precursor material 205 can initiate chemical crosslinking of the biopolymer. After the first and second precursor materials 203, 205 are mixed, chemical crosslinking of the biopolymer occurs for enough time to allow the resulting embolic element 230 be delivered to the aneurysm before becoming too viscous to move through the lumen of the conduit 116. In addition, the period of time during which chemical crosslinking of the biopolymer occurs can be short enough to reach a target deployed viscosity within a reasonable time (e.g., in the range of 10-60 minutes; or at most 40 minutes, 30 minutes, 20 minutes, or 10 minutes) after delivery. The target deployed viscosity can be high enough to cause an agglomeration of the embolic element 230 to remain within the internal volume of the aneurysm without reinforcing the neck.

In at least some cases, the biopolymer has a non-zero degree of chemical crosslinking within the first precursor material 203 before mixing with the chemical crosslinking agent. This can be useful, for example, to customize the curing window for the embolic element 230 so that it corresponds well with an expected amount of time needed to deliver the material to the aneurysm. The degree of chemical crosslinking of the biopolymer within the first precursor material 203 before mixing with the chemical crosslinking agent, the ratio of the biopolymer to the chemical crosslinking agent, and/or one or more other variables can be selected to cause the embolic element 230 to have a viscosity suitable for delivery to the aneurysm via the lumen of the conduit 116 for a suitable period of time (e.g., a period within a range from 10 minutes to 40 minutes) after mixing of the first and second precursor materials 203, 205. In at least some cases, the first and second precursor materials 203, 205 are mixed in proportions that cause a weight ratio of the biopolymer to the chemical crosslinking agent in the resulting embolic element 230 to be within a range from 10:1 to 100:1, such as from 10:1 to 30:1, or from 15:1 to 50:1, or from 15:1 to 25:1. In a particular example, the first and second precursor materials 203, 205 are mixed in proportions that cause a weight ratio of the biopolymer to the chemical crosslinking agent in the resulting embolic element 230 to be 30:1.

Use of a biopolymer instead of an artificial polymer in the first precursor material 203 may be advantageous because biopolymers tend to be more readily bioabsorbed than artificial polymers and/or for other reasons. Furthermore, use of a chemical crosslinking agent instead of a physical crosslinking agent (i.e., a crosslinking agent that forms noncovalent crosslinks between chains of the biopolymer) in the second precursor material 205 may be advantageous because chemically crosslinked polymers tend to be more cohesive than physically crosslinked polymers and/or for other reasons. In the context of forming a tissue scaffold within an aneurysm, high cohesiveness of the embolic element 230 may be more important than it is in other contexts to secure the cured embolic element 230 within the aneurysm 302. For example, high cohesiveness of the embolic element 230 may reduce or eliminate the possibility of a piece of the embolic element 230 breaking free and entering a patient's intracerebral blood stream during delivery.

The first and second precursor materials 203, 205 may include other components and/or the kit 200 may include other precursor materials intended for mixing with the first and second precursor materials 203, 205. For example, the first, second, and/or another precursor material may include a physical crosslinking agent. The presence of a physical crosslinking agent may be useful to form physical crosslinks that complement chemical crosslinks from the chemical crosslinking agent. The combination of chemical and physical crosslinks may enhance the cohesiveness of the embolic element 230. Suitable physical crosslinking agents for use with chitosan-based biopolymers include β glycerophosphate, mannitol, glucose, and derivatives and analogs thereof. In these and other cases, the embolic element 230 may include multiple chemical crosslinking agents and/or multiple physical crosslinking agents.

A contrast agent is another component that may be added to the precursor materials. The presence of a contrast agent within the embolic element 230 can be useful to visualize delivery of the embolic element 230 using fluoroscopy. One problem with using conventional platinum coils in intracranial aneurysms is that the persistent radiopacity of the coils tends to interfere with visualizing other aspects of the treatment in follow-up imaging. For example, the presence of platinum coils within an aneurysm may make it difficult or impossible to detect by fluoroscopy the presence of blood-carried contrast agent that would otherwise indicate recanalization. In at least some embodiments of the present technology, a contrast agent within the embolic element 230 is selected to provide radiopacity that diminishes over time. For example, the contrast agent may initially be radiopaque to facilitate delivery of the embolic element 230 and then become less radiopaque to facilitate follow-up imaging. In a particular example, the first, second, and/or another precursor material includes iohexol or a derivative or analog thereof as a suitable contrast agent.

In animal studies, the liquid embolics of the present technology were shown to provide (a) complete or nearly complete volumetric filling of the aneurysm internal volume, and (b) complete or nearly complete coverage of the aneurysm neck with new endothelial tissue. These features, among others, are expected to result in a lower recanalization rate than that of platinum coil treatments and faster aneurysm occlusion than that of flow diverters. Furthermore, the injectable scaffold material is expected to be bioabsorbed and thereby reduced in volume over time. Thus, unlike platinum coils, the injectable scaffold is expected to have little or no long-term mass effect. Furthermore, the injectable scaffold material can be configured to have diminishing radiopacity; therefore, when so configured it will not interfere future CT and MRI imaging and procedures. Embodiments of the present technology can have these and/or other features and advantages relative to conventional counterparts whether or not such features and advantages are described herein.

In some embodiments, the embolic kit 200 and/or embolic element 230 may be any embolic or occlusive device, such as one or more embolic coils, polymer hydrogel(s), polymer fibers, mesh devices, or combinations thereof. The embolic kit 200 may include one or more precursors that, once mixed together, form the embolic element 230 that remains within the aneurysm. In some embodiments, the embolic kit 200 may include the embolic element pre-mixed.

In some embodiments, the embolic kit 200 and/or embolic element 230 may be any embolic or occlusive device, such as one or more embolic coils, polymer hydrogel(s), polymer fibers, mesh devices, or combinations thereof. The embolic kit 200 may include one or more precursors that, once mixed together, form the embolic element 230 that remains within the aneurysm. In some embodiments, the embolic kit 200 may include the embolic element pre-mixed.

Additional details regarding suitable embolic elements may be found in U.S. patent application Ser. No. 15/299,929, filed Oct. 21, 2016, the disclosure of which is incorporated herein by reference in its entirety.

II. Selected Methods for Treating Aneurysms

FIGS. 3A-3G depict an example method for treating an aneurysm A with the systems 10 of the present technology. To begin, a physician may intravascularly advance the second elongated shaft 108 towards an intracranial aneurysm (or other treatment location such as any of those described herein) with the occlusive member 102 in a low-profile state. A distal portion of the second elongated shaft 108 may be advanced through a neck N of the aneurysm A to locate a distal opening of the second elongated shaft 108 within an interior cavity of the aneurysm A. The elongated member 106 may be advanced distally relative to the second elongated shaft 108 to push the occlusive member 102 through the opening at the distal end of the second elongated shaft 108, thereby releasing the occlusive member 102 from the shaft 108 and allowing the occlusive member 102 to self-expand into a first expanded state. Releasing the occlusive member 102 from the shaft 108 and allowing the occlusive member 102 to self-expand into a first expanded state may alternatively, or additionally, include withdrawing shaft 108 relative to the elongated member 106.

Figure 3A:
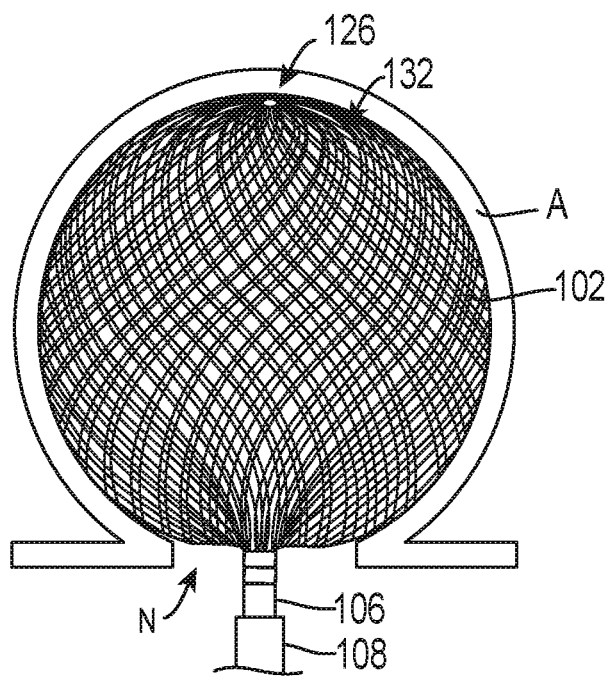
FIGS. 3A-3G depict an example method of treating an aneurysm with the treatment system of the present technology.
Figure 3B:
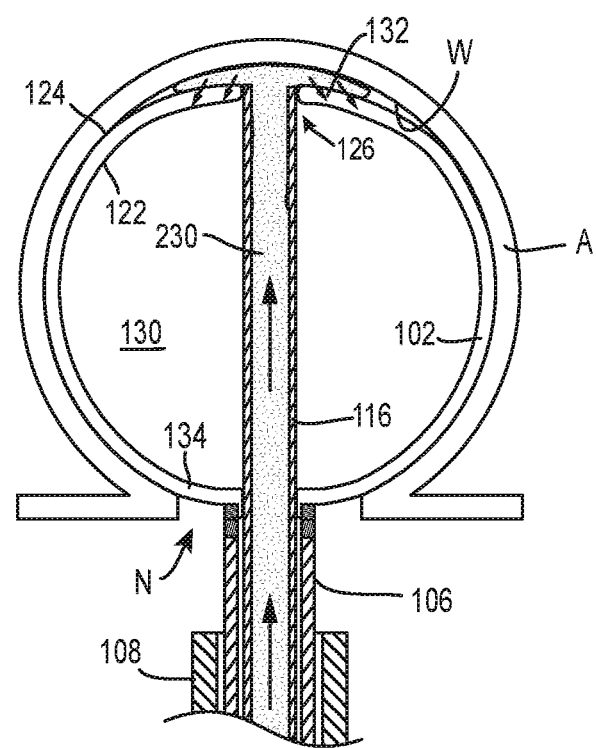

FIG. 3A shows the occlusive member 102 in a first expanded state, positioned in an aneurysm cavity and still coupled to the elongated member 106. As shown in FIG. 3A, in the first expanded state, the occlusive member 102 may assume a predetermined shape that encloses an internal volume 130 (see FIG. 1C). In this first expanded state, the occlusive member 102 may generally conform to the shape of the aneurysm A. As illustrated in FIG. 3B with the occlusive member 102 and delivery system shown in cross-section, the conduit 116 may be advanced through the internal volume 130 of the occlusive member 102 such that a distal opening of the conduit 116 is at or distal to the aperture 126 at the distal portion of the occlusive member 102. The embolic element 230 may be delivered through the conduit 116 to a space between the occlusive member 102 and an inner surface of the aneurysm wall W.

In some embodiments, the method includes mixing the first and second precursor materials 203, 205 (FIG. 2) to form the embolic element 230. Mixing of the first and second precursor materials 203, 205 may occur prior to introducing the embolic element 230 to the treatment system 100 and/or during delivery of the embolic element through the conduit 116 to the aneurysm. In a particular example, the first precursor material 203 is loaded into one of the barrels 214, the second precursor materials 205 is loaded into the other barrel 214, and the mixing syringes 208 are coupled via the coupler 210. To mix the first and second precursor materials 203, 205, the plungers 212 are alternately depressed, thereby causing the first and second precursor materials 203, 205 to move repeatedly from one barrel 214 to the other barrel 214. After suitably mixing the precursor materials, the resulting embolic element 230 can be loaded into the barrel 220 of the injection syringe 216. The injection syringe 216 may then be coupled to a proximal end of the conduit 116 to deliver the embolic element 230 through the conduit 116 and into the aneurysm A. As the embolic element 230 passes through the lumen of the conduit 116, chemical crosslinking of the biopolymer can continue to occur.

Figure 3C:
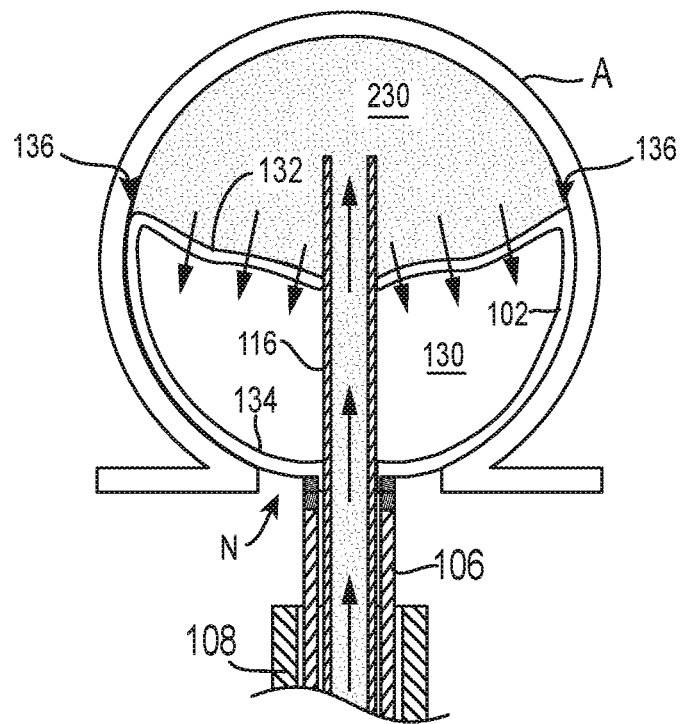
Figure 3D:
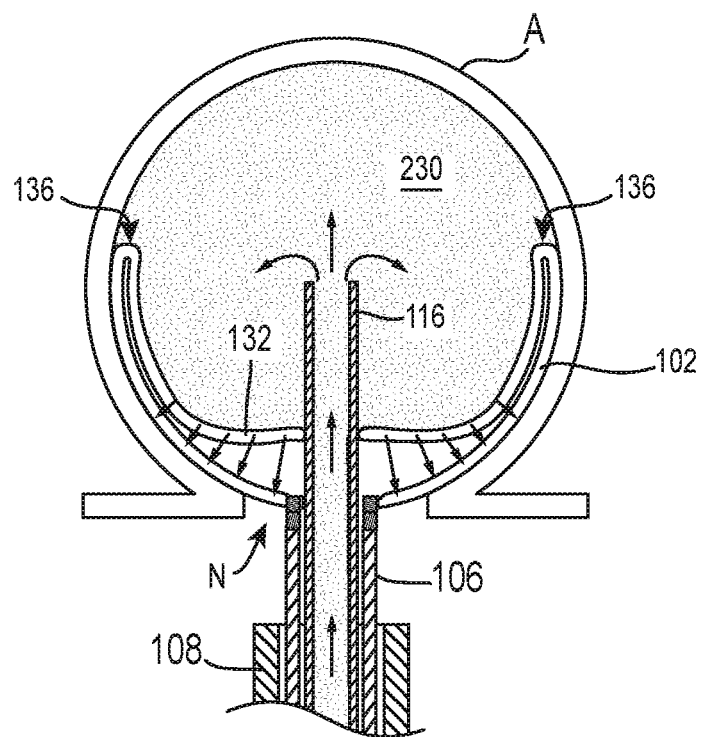

Still with reference to FIG. 3B, as the embolic element 230 is delivered between the dome of the aneurysm A and the distal portion 132 of the wall of the occlusive member 102, pressure builds between the aneurysm wall W and the occlusive member 102. As shown in the progression of FIGS. 3B-3D, when the forces on the occlusive member 102 reach a threshold level, the embolic element 230 pushes the distal wall 132 downwardly towards the neck N of the aneurysm A. The embolic element 230 exerts a substantially uniform pressure across the distal surface of the occlusive member 102 that collapses the occlusive member 102 inwardly on itself such that the rounded distal wall 132 transitions from concave towards the neck N of the aneurysm A to convex towards the neck N. The pressure and inversion of the distal portion of the wall 132 creates an annular fold 136 that defines the distal-most edge of the occlusive member 102. As the occlusive member 102 continues to invert, the position of the fold 136 moves towards the neck N, which continues until a distal-most half of the occlusive member 102 has inverted. In some embodiments, the occlusive member 102 may include one or more portions configured to preferentially flex or bend such that the occlusive member 102 folds at a desired longitude. Moreover, as the occlusive member 102 collapses, a distance between the wall at the distal portion 132 and the wall at the proximal portion decreases, and thus the internal volume 130 of the occlusive member 102 also decreases. As the occlusive member 102 collapses, the conduit 116 may be held stationary, advanced distally, and/or retracted proximally.

During and after delivery of the embolic element 230, none or substantially none of the embolic element 230 migrates through the pores of the occlusive member 102 and into the internal volume 130. Said another way, all or substantially all of the embolic element 230 remains at the exterior surface or outside of the occlusive member 102. Compression of the occlusive member with the embolic element 230 provides a real-time "leveling" or "aneurysm-filling indicator" to the physician under single plane imaging methods (such as fluoroscopy) so that the physician can confirm at what point the volume of the aneurysm is completely filled. It is beneficial to fill as much space in the aneurysm as possible, as leaving voids within the aneurysm sac may cause delayed healing and increased risk of aneurysm recanalization and/or rupture. While the scaffolding provided by the occlusive member 102 across the neck helps thrombosis of blood in any gaps and healing at the neck, the substantial filling of the cavity prevents rupture acutely and does not rely on the neck scaffold (i.e., the occlusive member 102). Confirmation of complete or substantially complete aneurysm filling under single plane imaging cannot be provided by conventional devices.

Once delivery of the embolic element 230 is complete, the conduit 116 may be withdrawn. In some embodiments, the embolic element 230 may fill greater than 40% of the aneurysm sac volume. In some embodiments, the embolic element 230 may fill greater than 50% of the aneurysm sac volume. In some embodiments, the embolic element 230 may fill greater than 60% of the aneurysm sac volume. In some embodiments, the embolic element may fill greater than 65%, 70%, 75%, 80%, 85%, or 90% of the aneurysm sac volume.

Figure 3E:
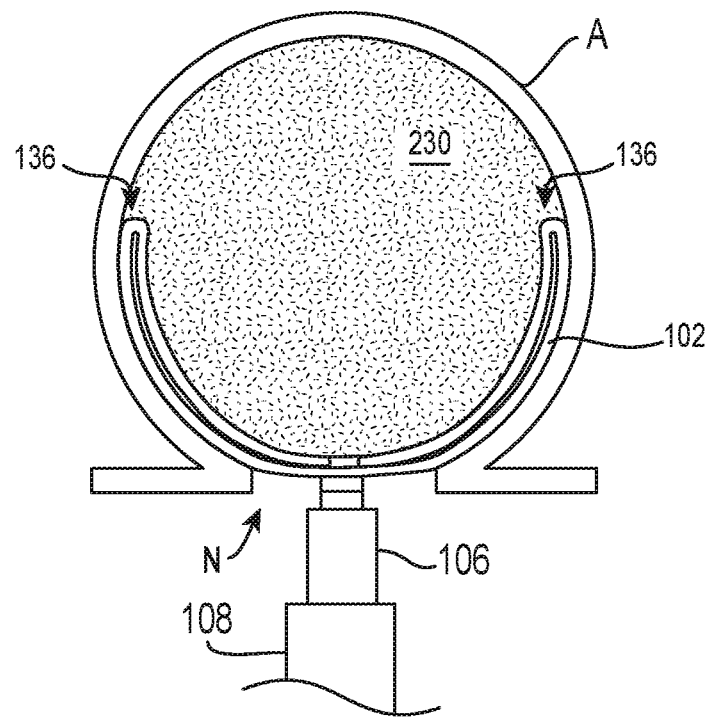
Figure 3F:
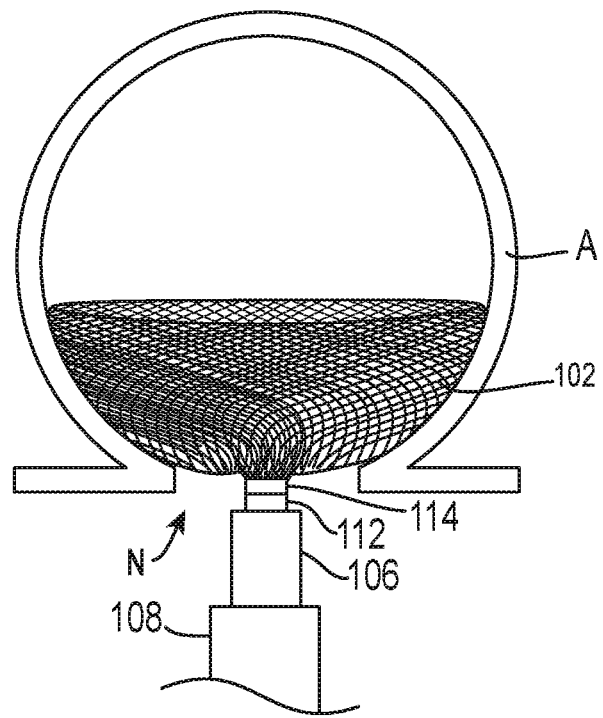

FIG. 3E shows a second expanded state of the occlusive member 102, shown in cross-section, with the embolic element 230 occupying the remaining volume of the aneurysm A. FIG. 3F shows the occlusive member 102 in full with the embolic element 230 removed so the second shape of the occlusive member 102 is visible. As shown, the embolic element 230 may be delivered until the occlusive member 102 is fully-collapsed such that the occlusive member 102 has substantially no internal volume.

In the second expanded state, the occlusive member 102 may form a bowl shape that extends across the neck of the aneurysm A. The wall of the occlusive member 102 at the distal portion may now be positioned in contact with or immediately adjacent the wall of the occlusive member 102 at the proximal portion. The distal wall 132 may be in contact with the proximal wall 134 along all or substantially all of its length. In some embodiments, the distal wall 132 may be in contact with the proximal wall 134 along only a portion of its length, while the remainder of the length of the distal wall 132 is in close proximity—but not in contact with—the proximal wall 134.

Collapse of the occlusive member 102 onto itself, towards the neck N of the aneurysm, may be especially beneficial as it doubles the number of layers across the neck and thus increases occlusion at the neck N. For example, the distal wall 132 collapsing or inverting onto the proximal wall 134 may decrease the porosity of the occlusive member 102 at the neck N. In those embodiments where the occlusive member 102 is a mesh or braided device such that the distal wall 132 has a first porosity and the proximal wall 134 has a second porosity, deformation of the distal wall 132 onto or into close proximity within the proximal wall 134 decreases the effective porosity of the occlusive member 102 over the neck N. The resulting multi-layer structure thus has a lower porosity than the individual first and second porosities. Moreover, the embolic element 230 along the distal wall 132 provides additional occlusion. In some embodiments, the embolic element 230 completely or substantially completely occludes the pores of the adjacent layer or wall of the occlusive member 102 such that blood cannot flow past the embolic element 230 into the aneurysm cavity. It is desirable to occlude as much of the aneurysm as possible, as leaving voids of gaps can allow blood to flow in and/or pool, which may continue to stretch out the walls of aneurysm A. Dilation of the aneurysm A can lead to recanalization and/or herniation of the occlusive member 102 and/or embolic element 230 into the parent vessel and/or may cause the aneurysm A to rupture. Both conditions can be fatal to the patient.

In those embodiments where the wall of the occlusive member 102 comprises an inner and outer layer, the deformed or second shape of the occlusive member 102 forms four layers over the neck N of the aneurysm A In those embodiments where the wall of the occlusive member 102 comprises a single layer, the deformed or second shape of the occlusive member 102 forms two layers over the neck N of the aneurysm A As previously mentioned, the neck coverage provided by the doubled layers provides additional surface area for endothelial cell growth, decreases the porosity of the occlusive member 102 at the neck N (as compared to two layers or one layer), and prevents herniation of the embolic element 230 into the parent vessel. During and after delivery, the embolic element 230 exerts a substantially uniform pressure on the occlusive member 102 towards the neck N of the aneurysm A, thereby pressing the portions of the occlusive member 102 positioned adjacent the neck against the inner surface of the aneurysm wall such that the occlusive member 102 forms a complete and stable seal at the neck N.

Figure 3G:
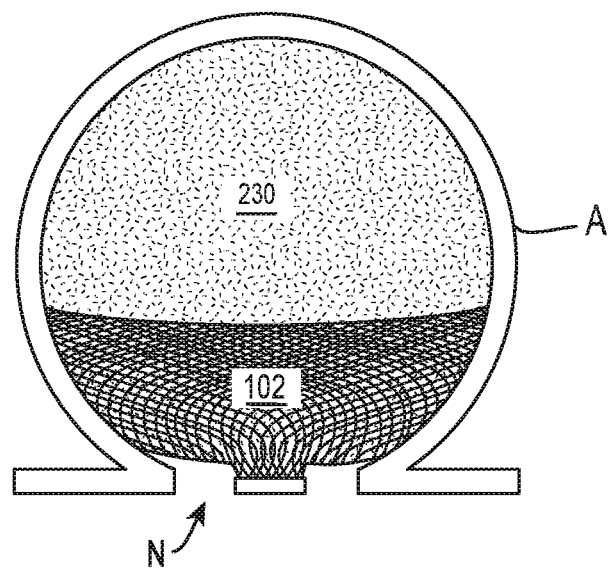

As shown in FIG. 3G, the first coupler 112 may be detached from the second coupler 114 and the elongated member 106 and second elongated shaft 108 may be withdrawn, thereby leaving the occlusive member 102 and embolic element 230 implanted within the aneurysm A. For example, the occlusive member 102 may be detached from the elongated member 106 using any of the mechanical detachment mechanisms described in more detail below.

Over time natural vascular remodeling mechanisms and/or bioabsorption of the embolic element 230 may lead to formation of a thrombus and/or conversion of entrapped thrombus to fibrous tissue within the internal volume of the aneurysm A. These mechanisms also may lead to cell death at a wall of the aneurysm and growth of new endothelial cells between and over the filaments or struts of the occlusive member 102. Eventually, the thrombus and the cells at the wall of the aneurysm may fully degrade, leaving behind a successfully remodeled region of the blood vessel.

In some embodiments, contrast agent can be delivered during advancement of the occlusive member 102 and/or embolic element 230 in the vasculature, deployment of the occlusive member 102 and/or embolic element 230 at the aneurysm A, and/or after deployment of the occlusive member 102 and/or embolic element 230 prior to initiation of withdrawal of the delivery system. The contrast agent can be delivered through the second elongated shaft 108, the conduit 116, or through another catheter or device commonly used to delivery contrast agent. The aneurysm (and devices therein) may be imaged before, during, and/or after injection of the contrast agent, and the images may be compared to confirm a degree of occlusion of the aneurysm.

According to some aspects of the technology, the system 10 may comprise separate first and second elongated shafts (e.g., microcatheters) (not shown), the first dedicated to delivery of the embolic element, and the second dedicated to the delivery of the occlusive member. In example methods of treating an aneurysm, the first elongated shaft may be intravascularly advanced to the aneurysm and through the neck such that that a distal tip of the first elongated shaft is positioned within the aneurysm cavity. In some embodiments, the first elongated shaft may be positioned within the aneurysm cavity such that the distal tip of the shaft is near the dome of the aneurysm.

The second elongated shaft containing the occlusive member (such as occlusive member 102) may be intravascularly advanced to the aneurysm and positioned within the aneurysm cavity adjacent the first elongated shaft. The occlusive member may then be deployed within the aneurysm sac. As the occlusive member is deployed, it pushes the first elongated shaft outwardly towards the side of the aneurysm, and when fully deployed the occlusive member holds or "jails" the first elongated shaft between an outer surface of the occlusive member and the inner surface of the aneurysm wall.

The embolic element (such as embolic element 230) may then be delivered through the first elongated shaft to a position between the inner surface of the aneurysm wall and the outer surface of the occlusive member. For this reason, it may be beneficial to initially position the distal tip of the first elongated shaft near the dome (or more distal surface) of the aneurysm wall. This way, the "jailed" first elongated shaft will be secured by the occlusive member such that the embolic element gradually fills the open space in the aneurysm sac between the dome and the occlusive member. As described elsewhere herein, the filling of the embolic element pushes and compresses the occlusive member against the tissue surrounding the aneurysm neck as the space in the sac above the occlusive member is being filled from the dome to the neck. Also as described elsewhere herein, the compression of the occlusive member with the embolic element provides a "leveling or aneurysm filling indicator" which is not provided by conventional single plane imaging methods. The filling of the embolic element may complete, for example, when it occupies about 50-80% of the volume of the aneurysm.

III. Example Interference Detachment Portions

Figure 4A:
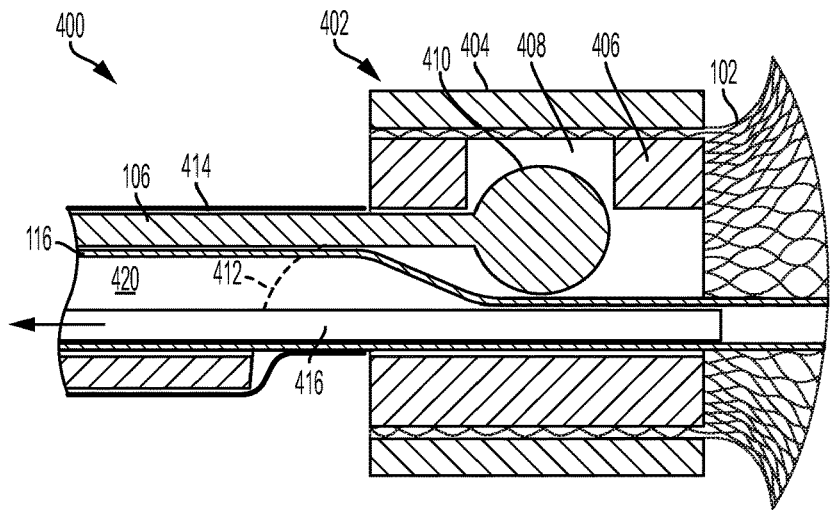
FIGS. 4A-4C are cross-sectional views of a detachment portion of a treatment system at different stages of detachment in accordance with aspects of the present technology.
Figure 4B:
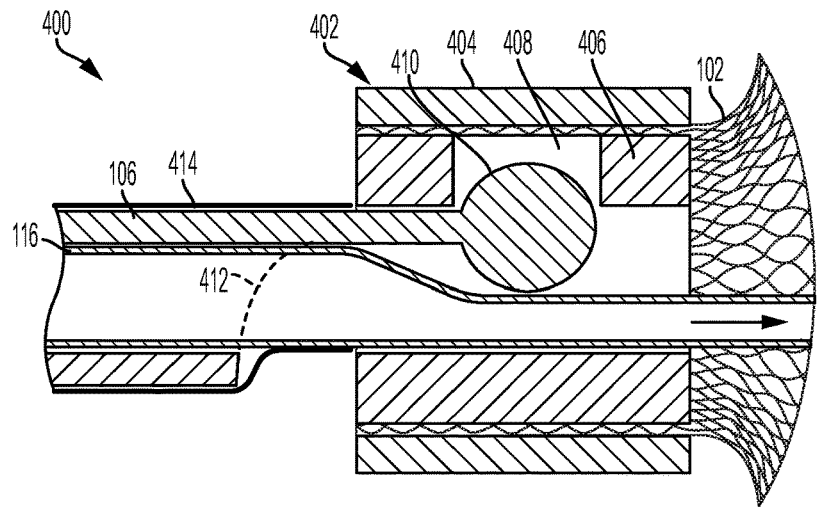
Figure 4C:
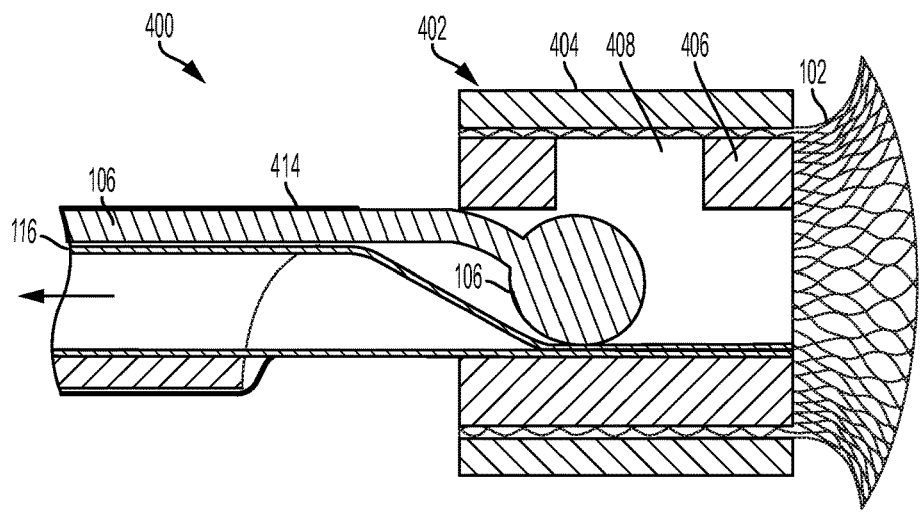

FIGS. 4A-4C show detailed views of a detachment portion 400 of a treatment system (e.g., treatment system 100 described previously herein) at different stages of detachment. As described in more detail below, the detachment portion 400 can include a mechanism to releasably secure the occlusive member 102 to a conduit for delivery of the occlusive member 102 to a treatment site and to facilitate conveyance of an embolic element to the treatment site, similar to the method described above with respect to FIGS. 3A-3G. As shown in FIG. 4, the elongate tubular member 106 can be coupled to the occlusive member 102 via a hub 402. The hub 402 includes an outer band 404 that surrounds the inner band 406, such proximal portions of the layers of the occlusive member 102 are grasped between the inner and outer bands 404, 406 of the hub 402. The hub 402 can include a recess 408, for example an aperture, window, or detent formed within the inner band 406. The recess 408 can extend around some or all of the inner band 406. In some embodiments, the recess 408 can assume other configurations, for example the recess can be disposed axially between two adjacent bands of the hub.

The elongate tubular member 106 can have an engagement member 410 configured to be releasably engaged (e.g., at least partially received within) the recess 408 of the hub 402. The engagement member 410 can be a ridge, projection, protrusion, enlargement, or any other suitable structure configured to be releasably engaged with the recess 408. In some embodiments, the engagement member 410 can have a rounded surface, for example being generally spherical or spheroidal. In some embodiments, the engagement member 410 can have at least a rounded proximal surface configured to contact a distal-facing surface of the recess 408. As such, when the engagement member 410 contacts the distal-facing surface of the recess 408, the curvature of the engagement member 410 can urge the engagement member 410 radially inwardly with respect to the hub 402. In some embodiments, the engagement member 410 can be disposed on a distal-most end of the elongated member 106.

In the illustrated embodiment, the elongated member 106 has a tapered distal edge 412 such that the engagement member 410 projects only away from one radial side of the elongated member 106. In some embodiments, the tapered distal edge can be formed by removing a portion of the tubular elongated member, such as a stainless steel hypotube, along at least an axially extending, distal portion of the tubular elongated member, such that the resulting portion of the elongated member no longer forms a closed tube and is more flexible than the original elongated member in the corresponding region. The engagement member 410 can then be formed or attached to the distal end of the elongated member. In other embodiments, the elongate member 106 can include a plurality of engagement members 410, any number of which can concurrently or separately engage with a recess or other suitable structure of the hub 402. In some embodiments, the engagement member 410 can extend partially or completely annularly around a circumference of the elongated member 106, for example an annular ridge or protrusion disposed over an outer surface of the elongated member 106 and configured to releasably engage the recess 408 of the hub 402.

The engagement member 410 may deflect radially inwardly to be separated or decoupled from the recess 408 of the hub 402. To maintain engagement with the hub 402, a control element 416 may be positioned radially adjacent to the engagement member 410 on a side opposite the portion of the recess 408 in which the engagement member 410 is received. The control element 416 may prevent radial deflection of the engagement member 410 away from the recess 408, therefore maintaining the engagement member 408 in a "locked" position with respect to the hub 402 and the occlusive member 102.

In some embodiments, the control element 416 comprises a wire, rod, shaft, or other elongated structure that can extend through the lumen of the elongate tubular member 106 to be removably positioned adjacent the engagement member 410. In some embodiments, the control element 416 can take the form of an elongated wire, for example made of nitinol, stainless steel, or any other suitable material. The control element 416 can be slidably removable such that, in a first position (as shown in FIG. 4A), the control element 416 is disposed radially adjacent to the engagement member 410 and prevents its decoupling from the hub 402.

A conduit 116 defining a lumen 420 therein can extend within a lumen of the elongate member 106. As noted previously, the conduit 116 can be an elongate, flexible tubular member configured to convey an embolic element (e.g., embolic element 230) therethrough for delivery to a treatment site. As shown in FIG. 4A, the control element 416 can be positioned within the lumen 420 of the conduit 116. The conduit lumen 420 can have a tapered diameter, for example having a smaller diameter at a distal portion configured to be positioned at or distal to the hub 402, and a larger diameter in a proximal portion configured to be positioned proximal to the hub 402. In other embodiments, the conduit lumen 420 can have a substantially uniform diameter along some or all of its length. As illustrated, the elongate member 106 can optionally have an exterior lining 414 disposed thereon to span over an outer surface of the elongate member 106 and over any exposed portion of the conduit 116. The lining 414 can take the form of tubing, and may extend over some or all of the length of the elongate member 106. In some embodiments, the lining 414 extends only over a distal portion of the elongate member 106, to extend over the tapered end 412 without covering the engagement member 410.

In the configurations shown in FIGS. 4B and 4C, the control element 416 has been removed, for example by being proximally retracted within the lumen 420 of the conduit 116. Once the control element 416 has been so moved, the embolic element 230 can be introduced through the lumen 420. Following introduction of the embolic element 230, proximal retraction of the elongated member 106 causes the engagement member 410 to abut the recess 408 and be deflected radially inwardly or otherwise out of engagement with the recess 408, and also deform the conduit 116. With continued proximal retraction of the elongate member 106, the engagement member 410 can be fully removed from the hub 402 and the elongated member 106 can be removed from the body, while the occlusive member 102 and hub 402 remain in position at the treatment site.

The engagement member 410, recess 408, and control element 416 illustrate one example of an interference mechanism that can be used to releasably secure the occlusive member 102 to the elongated member 106 and/or the conduit 116. In various embodiments, any number of interference mechanisms may be used. For example, instead of engaging with the recess 408, the engagement member 410 may extend distally beyond a distal end of the hub 402, or may engage with any other structural feature coupled to the occlusive member 102. The engagement member 410 and the control element 416 and the wall thickness of the conduit 116 adjacent the engagement member 410 can be configured such that the combined diameter of these elements is larger than a lumen of the hub 402, while the combined diameter of the engagement member 410 and the wall thickness of conduit 116 adjacent the engagement member 410 is smaller than a lumen of the hub 402, and accordingly while the control element 416 remains within the lumen of the hub 402, the engagement member 410 cannot be retracted therethrough. Once the control element 416 is removed, however, the engagement member 410 may be proximally retracted through the hub 402, causing the engagement member 410 to abut the recess 408 and be deflected radially inwardly or otherwise out of engagement with the recess 408 while also deforming conduit 116 to release the occlusive member 102. As another example, a plurality of control elements 416 can be used to provide the interference fit, rather than a single control element. Similarly, a plurality of engagement members 410 can be provided, rather than a single engagement member.

Figure 5A:
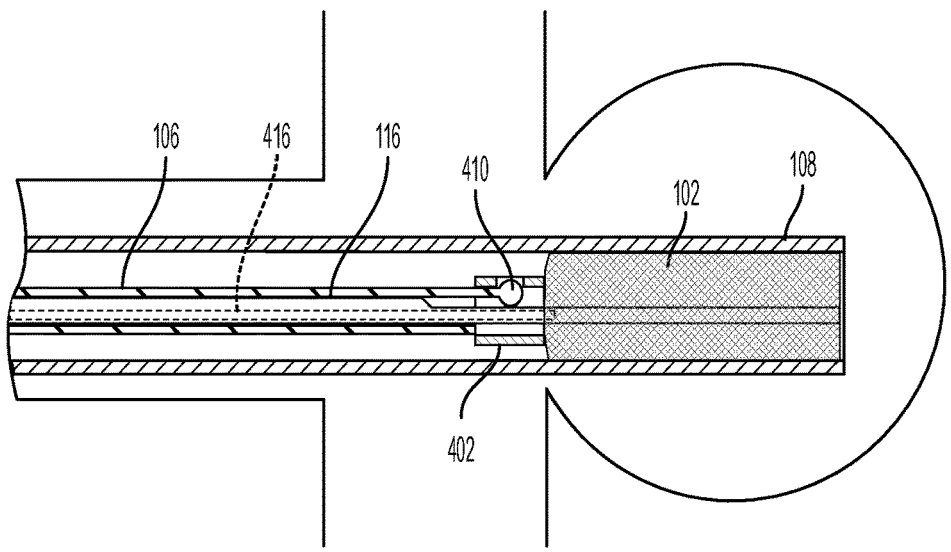
FIGS. 5A-5C illustrate delivery of an occlusive member and embolic element to a treatment site in accordance with aspects of the present technology.
Figure 5B:
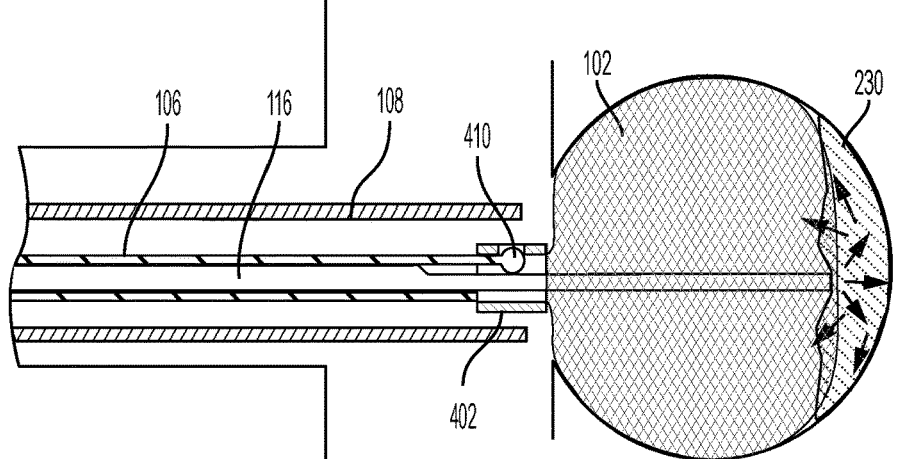
Figure 5C:
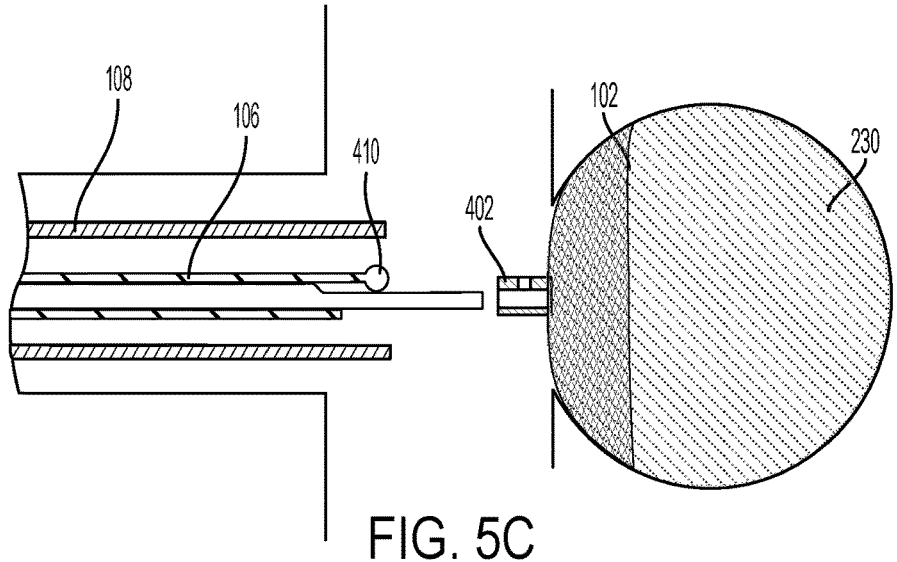

FIGS. 5A-5C illustrate delivery of an occlusive member 102 and embolic element 230 to a treatment site within an aneurysm sac. As shown in FIG. 5A, the system can be positioned within a second elongate shaft 108 (e.g., a microcatheter) for intravascular advancement until the microcatheter is at or adjacent to the aneurysm sac. In the illustrated embodiment, the distal end of the second elongate shaft 108 extends within the aneurysm sac, however in other embodiments the distal end of the second elongate shaft 108 can be positioned at the neck of the aneurysm or proximal to the neck of the aneurysm. In the position shown in FIG. 5A, the system has been advanced within the elongate shaft 108 such that the occlusive member 102 remains in a constrained, low-profile configuration within the shaft 108. In various embodiments, the shaft 108 can have an inner diameter of about 0.017 inches or less, about 0.021 inches or less, or about 0.027 inches or less.

As shown in FIG. 5B, once the distal opening of the conduit 116 is positioned at or near the treatment site (e.g., within the aneurysm sac), the elongate shaft 108 can be retracted, thereby deploying the occlusive member 102 within the aneurysm sac (e.g., allowing the occlusive member 102 to self-expand). Prior to, after, or concurrently with deploying the occlusive member 102, the control element 416 can be proximally retracted from within the lumen of the conduit 116. With the control element 416 removed, the embolic element 230 can be conveyed through the conduit 116 and into the aneurysm to a region distal to the occlusive member 102. In the case of a fluid or gel, a syringe or other injector may be used to urge the embolic element 230 through the lumen. In the case of microcoils or other structural embolic element(s), a delivery wire or other suitable mechanism may be slidably advanced through the lumen of the conduit to position the embolic element 230 into the aneurysm sac.

As described previously with respect to FIGS. 3A-3G, introduction of the embolic element 230 can cause the occlusive member 102 to deform, for example to at least partially fold in on itself to provide for increased protection in a neck region of the aneurysm. Once the embolic element 230 been delivered and the occlusive member 102 has deformed, the occlusive member 102 can detached from the elongate member 106 as described above with respect to FIGS. 4A-4C. For example, the elongate member 106 can be retracted, thereby permitting the engagement member 410 to at least temporarily deflect away from the hub 402. Because the control element 416 has been removed previously, the engagement member 410 may disengage from the recess 408 and deform the conduit 116 upon retraction of the elongate member 106, without any interference or resistance from the control element 416.

As shown in FIG. 5C, after the occlusive member 102 is decoupled from the second elongated member 106, the elongated member 106 and the surrounding elongate shaft 108 can be proximally retracted. Alternatively, the elongated member 106 can be proximally retracted into the surrounding elongate shaft 108. Following this separation, the occlusive member 102 and the embolic element 230 may remain positioned within the aneurysm.

Figure 6A:
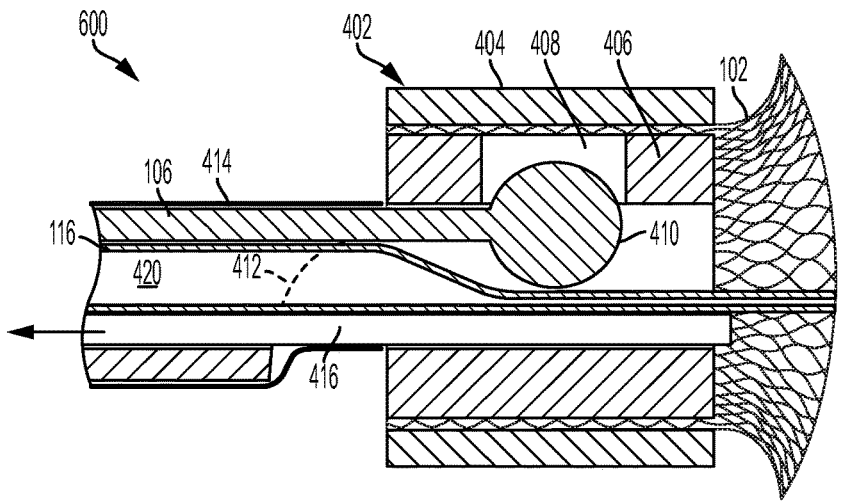
FIGS. 6A-6C are cross-sectional views of another embodiment of a detachment portion of a treatment system at different stages of detachment in accordance with aspects of the present technology.
Figure 6B:
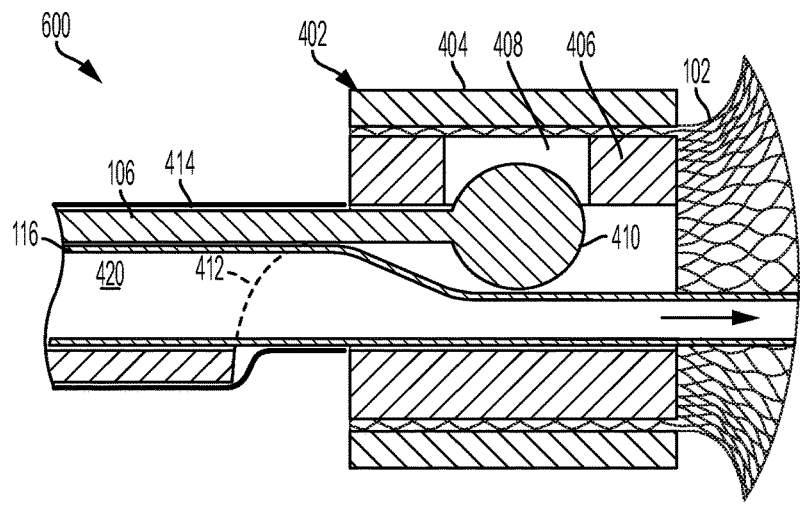
Figure 6C:
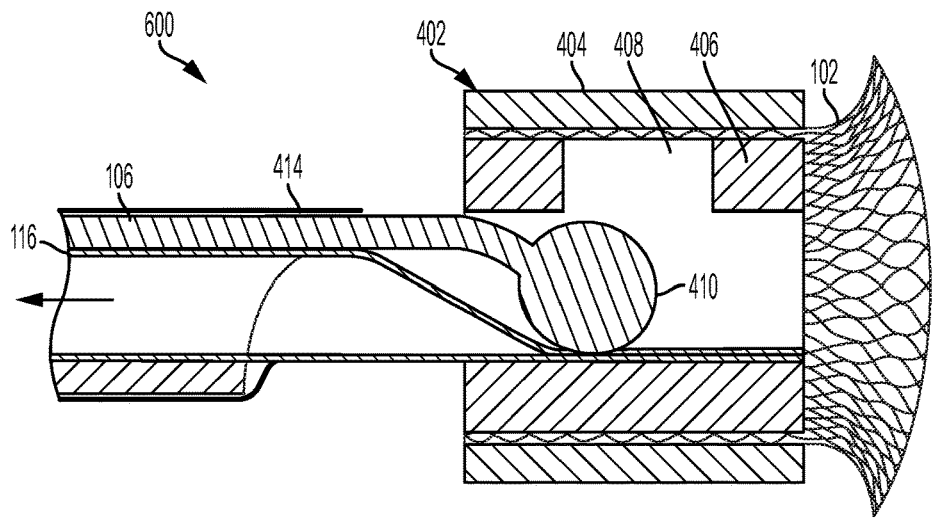

FIGS. 6A-6C illustrate another embodiment of a detachment portion 600. Here, the control element 416 extends within the lumen of the elongate member 106, but is disposed outside of the lumen 420 of the conduit 116. In this configuration, the presence of the control element 416 may effectively collapse the lumen 420 of the conduit 116 in the region radially adjacent to the engagement member 410, thereby urging the engagement member 410 into a locked or engaged position with the recess 408 of the hub 402. In operation, the control element 416 can be removed (e.g., proximally retracted) after positioning the occlusive member 102 at the treatment site, after which the lumen 420 of the conduit 116 may resume its open state, such as upon introduction of an embolic element therethrough. As shown in FIG. 6B, in this state, an embolic element may be conveyed through the lumen 420 and delivered to the treatment site. Once the occlusive member 102 and any embolic element(s) have been delivered, the elongated member 106 can be proximally retracted, thereby causing the engagement member 410 to deflect radially inwardly and out of engagement with the recess 408 of the hub 402 while also deforming the conduit 116, as depicted in FIG. 6C. Prior to, after, or concurrently with deploying the occlusive member 102, the control element 416 can be proximally retracted from within the lumen of the elongated member 106.

Figure 7:
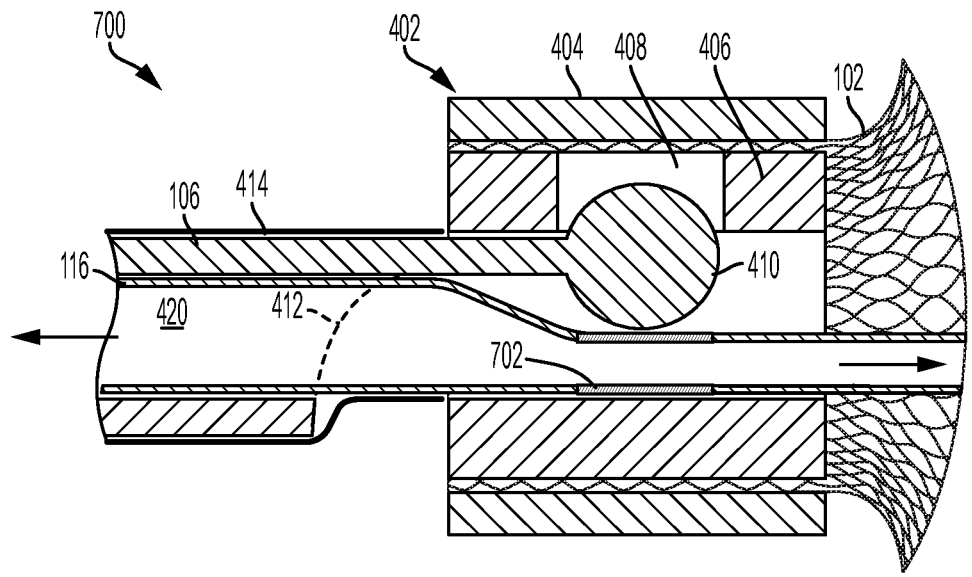
FIG. 7 illustrates another embodiment of a detachment portion of a treatment system in accordance with aspects of the present technology.

FIG. 7 illustrates another embodiment of a detachment portion 700. Here, a restraint 702 is coupled to or integrated within a portion of the conduit 116 that is configured to be disposed radially adjacent to the engagement member 410. The restraint 702 can be configured to exert a radially outward force, thereby urging the engagement member 410 towards the recess 408 of the hub. The restraint 702 can be a radially outwardly biased member, for example a stent, braid, coil, etc., that has been positioned within the lumen 420 of the conduit 116 and configured to provide sufficient hoop strength to maintain the engagement member 410 in the locked or engaged configuration. Alternatively or additionally, the restraint 702 can comprise a reinforced portion of the wall of the conduit 116, for example having increased wall thickness, embedded metallic reinforcements, or other structural features that resist deformation and maintain the engagement member 410 in the "locked" configuration at least partially received within the recess 408.

To release the engagement member 410 from its locked position, the conduit 116 can be either slidably advanced distally or retracted proximally such that the restraint 702 is not axially aligned with the engagement member 410. This axial displacement of the restraint 702 can occur before, during, or after introduction of an embolic element through the lumen 420 of the conduit 116 to the treatment site. Once the restraint is no longer axially aligned with the engagement member, proximal retraction of the elongate member 106 causes the engagement member 410 to contact the sidewall of the recess 408 and deflect radially inwardly to decouple from the hub 402.

Figure 8:
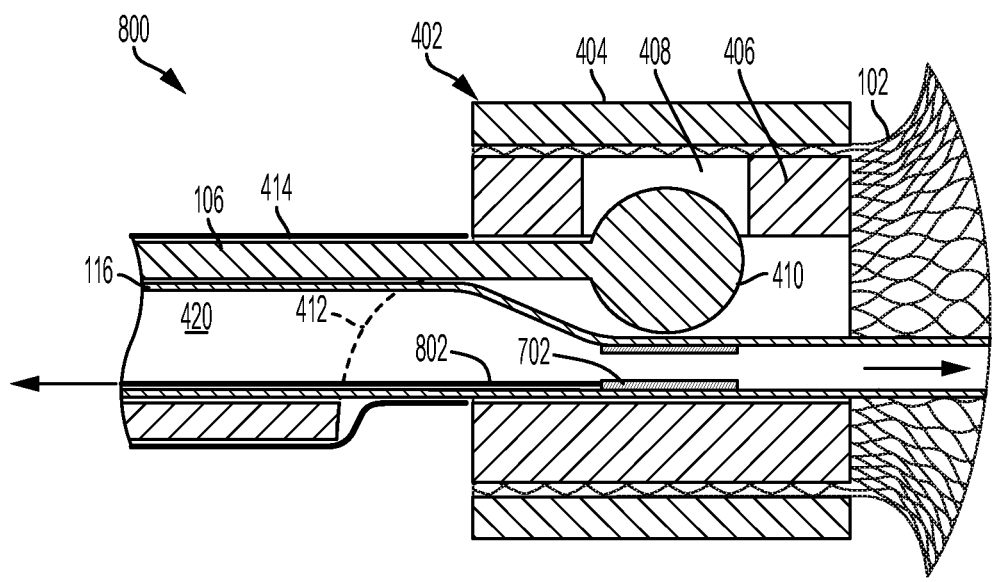
FIG. 8 illustrates another embodiment of a detachment portion of a treatment system in accordance with aspects of the present technology.

In the detachment portion 800 illustrated in FIG. 8, the restraint 702 is coupled to a pull wire 802 such that it can be removed or at last axially displaced while the conduit 116 remains in position. In this configuration, the pull wire 802 can be proximally retracted, thereby removing the restraint 702, or at least positioning the restraint 702 at least partially proximal to the engagement member 410. In this state, the engagement member 410 may be able to deflect radially inwardly away from the recess 408, even while the conduit 116 remains in place. Accordingly, proximally retracting the elongated member 106 and the engagement member 410 can release the engagement member 410 from the recess 408 while also deforming the conduit 116, and allow for removal of the engagement member 106 and the conduit 116 from the treatment site.

Advantageously, in using either the detachment portion 700 or 800, the occlusive member 102 can remain fixedly secured to the elongated member 106 and the conduit 116 can remain in place during delivery of the embolic element therethrough to the treatment site. The clinician need not initiate decoupling the elongated member 106 and/or the conduit 116 from the occlusive member 102 until after the embolic element has been fully deployed and the occlusive member 102 has achieved its final position.

IV. Example Threaded Detachment Portions

Figure 9A:
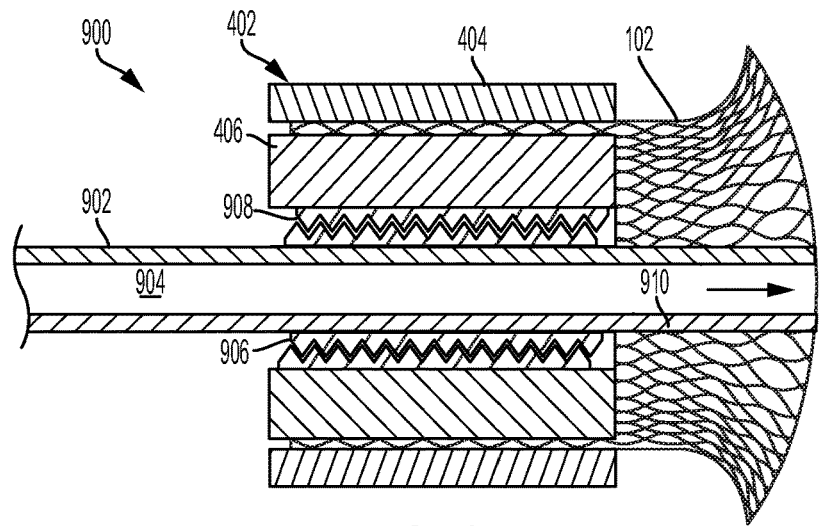
FIGS. 9A-9C are cross-sectional views of another embodiment of a detachment portion of a treatment system at different stages of detachment in accordance with aspects of the present technology.
Figure 9B:
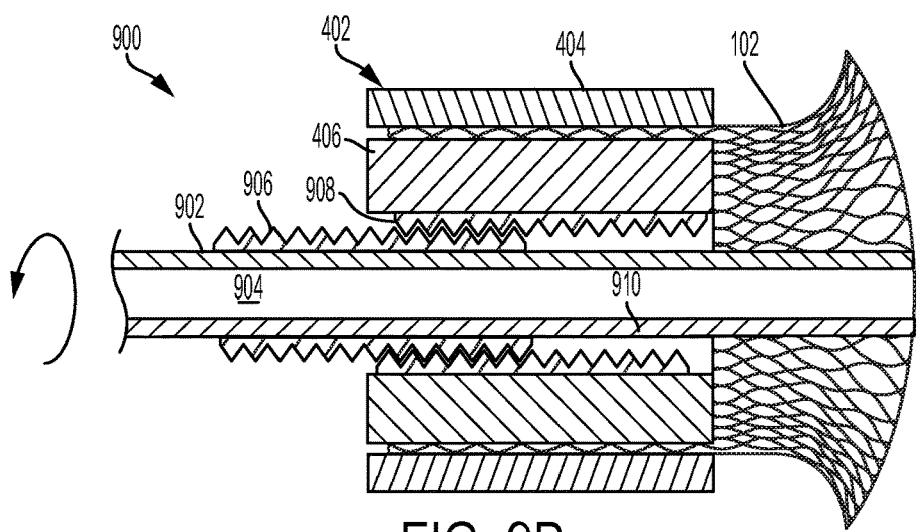
Figure 9C:
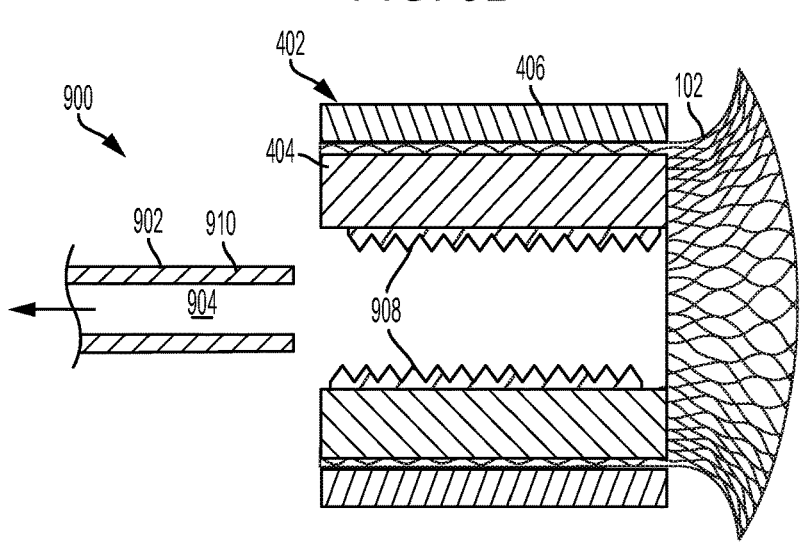

FIGS. 9A-9C illustrate a threaded detachment portion 900 at various stages of detachment. As shown, the detachment portion 900 includes a conduit 902 removably coupled to the hub 402 via threaded engagement. The conduit 902 can be a hypotube, microcatheter, or other suitable tubular member having a lumen 904 configured to convey an embolic element (e.g., embolic element 230) therethrough for delivery to a treatment site. The conduit 902 includes an engagement portion 906, which can take the form of comprising radially outwardly facing threads (e.g., male threads). The threads can be formed as protrusions extending away from the outer surface of the conduit 902 or as recesses formed into an outer surface of the conduit 902. In some embodiments, the threads can be a discrete component adhered to or otherwise fastened to the outer surface of the conduit 902. For example, the threads can be coupled to a bushing that is fitted over and adhered to the outer surface of the conduit 902. The engagement portion 906 of the conduit 902 Can be configured to releasably mate with a corresponding engagement portion 908 of the hub 402, which may take the form of radially inwardly facing threads (e.g., female threads) disposed on a radially inner surface of the inner band 406 of the hub 402. Additionally or alternatively, any other pairs of suitable mechanically interlocking structures can be used in lieu of threads.

The conduit 902 can include a distal portion 910 that extends distally beyond the engagement portion 906. In the coupled configuration (shown in FIG. 9A), the distal portion 910 extends distally with respect to the hub 402. In some embodiments, the distal portion 910 can terminate at a distal end (not shown) that is at, near, or distal to a distal end of the occlusive member 102 while in the expanded state. In this orientation, an embolic element delivered through the lumen 904 of the conduit 902 can be conveyed to a region distal to the expanded occlusive member 102.

After delivery of the embolic element through the lumen 904, the conduit 902 can be released from the hub 402 by rotation of the conduit 902 with respect to the hub 402, as shown in FIGS. 9B and 9C. Once fully disengaged, the conduit 902 can be removed from the body (e.g., by being proximally retracted through a surrounding guide catheter) and the occlusive member 102 and hub 402 can remain in position within the body.

One advantage of such threaded detachment mechanisms is that the occlusive member 102 can remain fixedly secured to the conduit 902 during delivery of the embolic element therethrough to the treatment site. The clinician need not initiate decoupling the conduit 902 from the occlusive member 102 until after the embolic element has been fully deployed and the occlusive member 102 has achieved its final position. At this stage, the conduit 902 can be rotated (e.g., by grasping a proximal end portion of the conduit 902 and rotating it by hand with machine assistance) to disengage the threads of the engagement portion 906 with the corresponding threads of the engagement portion 908.

Figure 10A:
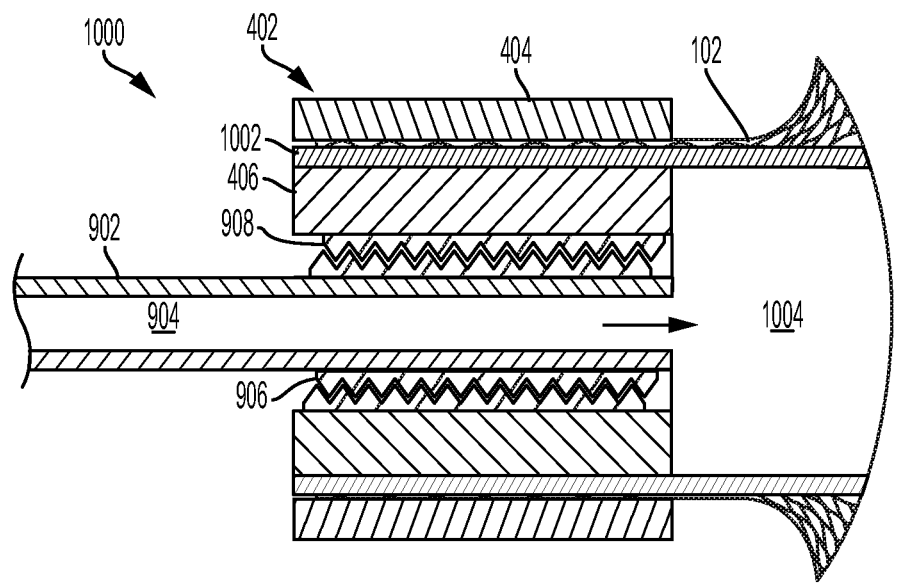
FIGS. 10A and 10B are cross-sectional views of another embodiment of a detachment portion of a treatment system at different stages of detachment in accordance with aspects of the present technology.
Figure 10B:
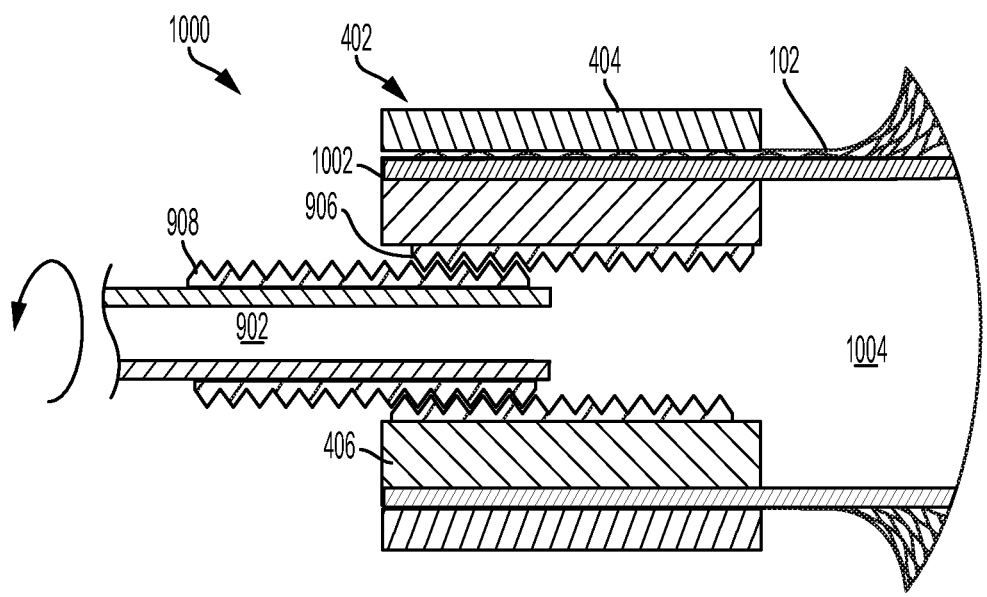

FIGS. 10A and 10B illustrate another embodiment of a threaded detachment portion 1000 at various stages of detachment. In the illustrated embodiment, the conduit 902 takes the form of a proximal conduit 902, again having an engagement portion 906 in the form of male threads configured to mate with a corresponding engagement portion 908 in the form of female threads carried by the inner band 406 of the hub 402. However, in this embodiment, the proximal conduit 902 terminates at or near a distal end of the engagement portion 906, which, in the coupled configuration, may also be at or near a distal end of the hub 402. In some embodiments, the engagement portion 906 can include threads that are formed as recesses in an outer surface of the conduit 902, as opposed to projections that extend away from an outer surface of the conduit 902. As such, the overall outer dimensions can be reduced, as the hub 402 can have a smaller radial dimension to engage with the engagement portion 906 of the conduit 902.

A distal conduit 1002 can be non-removably coupled to the hub 402, for example being at least partially secured between the inner band 406 and outer band 404 of the hub 402. The distal conduit 1002 can be an elongate tubular member extending through some or all of the length of the occlusive member 102. The distal conduit 1002 can be made of a biocompatible material, for example PTFE, stainless steel, nitinol, or any other suitable material. In operation, while the proximal conduit 902 is coupled to the hub 402, the lumen 904 of the proximal conduit is in fluid communication with the lumen 1004 of the distal conduit 1002, thereby providing a common lumen through which an embolic element (e.g., embolic element 230) can be delivered to the treatment site.

After delivery of the embolic element through the lumens 904 and 1004, the conduit 902 can be released from the hub 402 by rotation of the conduit 902 with respect to the hub 402, as shown in FIG. 10B. Once fully disengaged, the conduit 902 can be removed from the body (e.g., by being proximally retracted through a surrounding guide catheter), leaving the occlusive member 102, the hub 402, and the distal conduit 1002 in position within the body.

V. Conclusion

Although many of the embodiments are described above with respect to systems and methods related to treatment of hemorrhagic stroke, the technology is applicable to other applications and/or other approaches. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 1A-10B.

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

Unless otherwise indicated, all numbers expressing dimensions, percentages, or other numerical values used in the specification and claims, are to be understood as being modified in all instances by the term "about." Accordingly, unless indicated to the contrary, the numerical parameters set forth in the specification and attached claims are approximations that may vary depending upon the desired properties sought to be obtained by the present technology. At the very least, and not as an attempt to limit the application of the doctrine of equivalents to the scope of the claims, each numerical parameter should at least be construed in light of the number of reported significant digits and by applying ordinary rounding techniques. Additionally, all ranges disclosed herein are to be understood to encompass any and all subranges subsumed therein. For example, a range of "1 to 10" includes any and all subranges between (and including) the minimum value of 1 and the maximum value of 10, i.e., any and all subranges having a minimum value of equal to or greater than 1 and a maximum value of equal to or less than 10, e.g., 5.5 to 10.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

The invention claimed is:

1. A treatment system comprising:
an occlusive implant configured to be positioned within an aneurysm sac, the occlusive implant comprising a hub;
an elongate tubular member having a sidewall defining a first lumen extending therethrough and an engagement member as a distal extension of the sidewall and releasably engaged with the hub;
a control element configured to extend within the first lumen and to urge the engagement member into engagement with the hub; and
a conduit extending within the first lumen, the conduit defining a second lumen configured to receive a liquid embolic therethrough for delivery to the aneurysm sac.

2. The treatment system of claim 1, wherein the engagement member is removably coupled to the hub via an interference fit.

3. The treatment system of claim 1, wherein the hub has a recess, and the engagement member comprises a protrusion configured to be removably received within the recess.

4. The treatment system of claim 1, wherein the control element comprises a wire or rod configured to restrain the engagement member from decoupling from the hub.

5. The treatment system of claim 1, wherein the control element is slidably removable from the first lumen.

6. The treatment system of claim 1, further comprising a restraint disposed radially adjacent the engagement member, the restraint configured to exert a radially directed force on the engagement member.

7. The treatment system of claim 1, wherein the occlusive member comprises an expandable mesh having a constrained state for delivery to the aneurysm and an expanded state in which at least a portion of the mesh is configured to be disposed across a neck of the aneurysm.

8. The treatment system of claim 1, wherein the control element extends within the second lumen.

9. The treatment system of claim 1, wherein the occlusive implant comprises an expandable mesh having a constrained state for delivery to the aneurysm sac and an expanded state in which at least a portion of the mesh is configured to be disposed across a neck of the aneurysm.

10. The treatment system of claim 9, wherein the expandable mesh comprises a plurality of braided filaments that assume a pre-set, three-dimensional shape in the expanded state.

11. A treatment system comprising:
  an occlusive member configured to be positioned at or adjacent a treatment site;
  an elongate tubular member having a sidewall defining a first lumen and an engagement member extending axially from the sidewall and removably coupled to the occlusive member;
  a control element configured to extend within the first lumen and to urge the engagement member into engagement with the occlusive member; and
  a conduit extending within the first lumen, the conduit defining a second lumen configured to receive a liquid embolic therethrough.

12. The treatment system of claim 11, wherein the engagement member is removably coupled to a hub of the occlusive member via an interference fit.

13. The treatment system of claim 12, wherein the hub has a recess, and the engagement member comprises a protrusion configured to be removably received within the recess.

14. The treatment system of claim 11, wherein the control element comprises a wire or rod configured to restrain the engagement member from decoupling from the occlusive member.

15. The treatment system of claim 11, wherein the control element is slidably removable from the first lumen.

16. The treatment system of claim 11, further comprising a restraint disposed radially adjacent the engagement member, the restraint configured to exert a radially directed force on the engagement member.

17. The treatment system of claim 11, wherein the control element extends within the second lumen.

18. The treatment system of claim 11, wherein the occlusive implant comprises an expandable mesh having a constrained state for delivery to an aneurysm and an expanded state in which at least a portion of the mesh is configured to be disposed across a neck of the aneurysm.

19. The treatment system of claim 18, wherein the expandable mesh comprises a plurality of braided filaments that assume a pre-set, three-dimensional shape in the expanded state.

* * * * *